(12) United States Patent
Calderwood et al.

(10) Patent No.: US 10,426,445 B2
(45) Date of Patent: Oct. 1, 2019

(54) SAMPLE COLLECTION AND TRANSFER ASSEMBLY AND RELATED METHODS

(71) Applicant: Advanced Animal Diagnostics, Inc., Morrisville, NC (US)

(72) Inventors: David A. Calderwood, Chapel Hill, NC (US); Joy Parr Drach, Pontiac, IL (US); Chris Paul, Hillsborough, NC (US); Rodolfo R. Rodriguez, Cary, NC (US); Mitch Hockett, Raleigh, NC (US); Randall Marcuson, Creedmor, NC (US); Stephen G. Miggels, Wyckoff, NJ (US); Demetris Young, Durham, NC (US)

(73) Assignee: Advanced Animal Diagnostics, Inc., Morrisville, NC (US)

( * ) Notice: Subject to any disclaimer, the term of this patent is extended or adjusted under 35 U.S.C. 154(b) by 878 days.

(21) Appl. No.: 14/394,900

(22) PCT Filed: Jun. 20, 2013

(86) PCT No.: PCT/US2013/046760
§ 371 (c)(1),
(2) Date: Oct. 16, 2014

(87) PCT Pub. No.: WO2013/192396
PCT Pub. Date: Dec. 27, 2013

(65) Prior Publication Data
US 2015/0126904 A1    May 7, 2015

Related U.S. Application Data

(60) Provisional application No. 61/757,466, filed on Jan. 28, 2013, provisional application No. 61/696,517, (Continued)

(51) Int. Cl.
*A61B 10/00* (2006.01)
*A01J 5/04* (2006.01)
(Continued)

(52) U.S. Cl.
CPC .......... *A61B 10/0045* (2013.01); *A01J 5/045* (2013.01); *A61B 90/90* (2016.02); *A61B 90/94* (2016.02);
(Continued)

(58) Field of Classification Search
CPC ................................................ A61B 10/0045
See application file for complete search history.

(56) References Cited

U.S. PATENT DOCUMENTS 4,722,598 A * 2/1988 Ford ...................... G02B 21/34
356/246
5,865,347 A * 2/1999 Welschoff ........... B05B 11/0054
222/137

(Continued)

FOREIGN PATENT DOCUMENTS

EP    1 380 345    1/2004
EP    2 264 424    12/2010
(Continued)

OTHER PUBLICATIONS

International Search Report and Written Opinion for PCT/US2013/046760 dated Jun. 20, 2013.

*Primary Examiner* — Daniel L Cerioni
*Assistant Examiner* — Yasmeen S Warsi
(74) *Attorney, Agent, or Firm* — Myers Bigel, P.A.

(57) ABSTRACT

A collection device includes a base housing member having at least one chamber. A cover housing member has at least one aperture therein, and the cover housing member is configured to cover the base housing member such that the at least one aperture is positioned in fluid communication
(Continued)

with the at least one chamber. The cover housing member includes a cartridge holding interface configured to releasably engage with a cartridge that is configured to cover and receive a fluid from the at least one chamber via the at least one aperture.

26 Claims, 21 Drawing Sheets

Related U.S. Application Data filed on Sep. 4, 2012, provisional application No. 61/662,158, filed on Jun. 20, 2012.

(51) Int. Cl.
| | |
|---|---|
| B01L 3/00 | (2006.01) |
| G01N 1/10 | (2006.01) |
| A61B 90/96 | (2016.01) |
| A61B 90/90 | (2016.01) |
| A61B 90/94 | (2016.01) |
| A61B 90/98 | (2016.01) |
| G01N 1/28 | (2006.01) |
| G01N 33/04 | (2006.01) |

(52) U.S. Cl.
CPC .............. *A61B 90/96* (2016.02); *A61B 90/98* (2016.02); *B01L 3/502* (2013.01); *G01N 1/10* (2013.01); *B01L 2300/046* (2013.01); *B01L 2300/047* (2013.01); *B01L 2300/0663* (2013.01); *B01L 2400/0406* (2013.01); *B01L 2400/0457* (2013.01); *G01N 1/2813* (2013.01); *G01N 33/04* (2013.01)

(56) References Cited

U.S. PATENT DOCUMENTS

2012/0106811 A1    5/2012    Chen et al.
2013/0172698 A1*    7/2013    Reynolds ........... A61B 5/14532
                                                           600/316

FOREIGN PATENT DOCUMENTS

| WO | WO 02/48681 | 6/2002 | |
|---|---|---|---|
| WO | WO 0248681 A2 * | 6/2002 | ........... G01N 1/2813 |
| WO | WO 03/009776 | 2/2003 | |

* cited by examiner

SAMPLE COLLECTION AND TRANSFER ASSEMBLY AND RELATED METHODS

RELATED APPLICATIONS

This application is a 35 U.S.C. § 371 national phase entry of PCT Application PCT/US2013/046760, filed Jun. 20, 2013, and published in English on Dec. 27, 2013, as International Publication No. WO 2013/1192396, which claims the benefit of U.S. Provisional Applications No. 61/662,158, filed Jun. 20, 2012, No. 61/696,517, filed Sep. 4, 2012, and No. 61/757,466, filed Jan. 28, 2013, the disclosures of which are incorporated by reference herein in their entirety.

FIELD OF THE INVENTION

The present invention relates to sample collection assembly including a sample collection and transfer device and a sample cartridge.

BACKGROUND

Mastitis is the inflammation of the mammary gland caused by microorganisms that invade one or more quadrants of the bovine udder, multiply, and produce toxins that are harmful to the mammary gland. Economic loss to mastitis in the United States is estimated to be over $2 billion. This is approximately 10% of the total value of farm milk sales, and about two-thirds of this loss is due to reduced milk production in subclinically infected cows.

In subclinical mastitis, there may be no visible signs of the disease, and diagnosis of subclinical mastitis may be performed by a somatic cell count (SCC) of the milk. The SCC is the number of leukocytes or white blood cells per volume of milk and is also used as an index of milk quality. It has also been recognized that there are multiple types of leukocytes, each with its own significance. In milk from a healthy animal, the predominant cell types are lymphocytes, followed by lesser numbers of neutrophils and macrophages. The percentages of each kind of cell rise and fall as part of the immune response to infection. Those percentages, "the milk leukocyte differential", cell count represent the unique immune status of an individual quarter udder, at a specific point in time for better diagnosis of subclinical mastitis.

One method for detecting the milk leukocyte differential is using flow-cytometry, which is an expensive, sophisticated tool typically only found in top research laboratories and generally not practical for the farmer. Another method for detecting the milk leukocyte differential is the "manual milk differential smear" (MMDS), which is a difficult and time consuming procedure, and is subject to great variability, even when performed by highly trained laboratory technologists. Both flow-cytometry and MMDS present practical difficulties for field research or a barn environment.

U.S. Patent Application Publication No. 2009/0233329 to Rodriguez discloses a wedge microfluidic slide chamber for detecting mastitis or other diseases from a body fluid of a mammal, such as from cow's milk. The wedge-shaped chamber uses capillary action to fill the chamber with the sample as a "self-preparing wet smear" with a meta-chromatic stain. The wedge-shaped microscope slide with the stained sample may be analyzed by visual identification and direct observation or by imaging instruments using computer-enhanced digital camera images. Accordingly, mastitis may be detected more easily with such a self-preparing wet smear.

Milk collection techniques for such a slide, however, may be time consuming and/or difficult. Typically, a sample from each quadrant of the cow's udder may be collected in different containers and pipetted by an operator into the wedge-shaped slide chamber for further analysis, for example, by an imaging instrument or reader. Moreover, it may be desirable to pipette the sample into the self-preparing wet smear relatively soon before placing the microscope slide into the imaging instrument or reader. The liquid samples may be stored in separate containers prior to analysis, and the tracking and/or storage of such samples may present various challenges, for example, to track which sample came from which cow and from which quadrant of the cow.

SUMMARY OF EMBODIMENTS OF THE INVENTION

In some embodiments, a collection device includes a base housing member having at least one chamber. A cover housing member has at least one aperture therein, and the cover housing member is configured to cover the base housing member such that the at least one aperture is positioned in fluid communication with the at least one chamber. The cover housing member includes a cartridge holding interface configured to releasably engage with a cartridge that is configured to cover and receive a fluid from the at least one chamber via the at least one aperture.

In some embodiments, the cartridge holding interface comprises a retaining wall or pins configured to abut an outer perimeter of the cartridge. The cartridge holding interface may include at least one notch and/or groove that is configured to engage a corresponding notch and/or groove on the cartridge. The cartridge holding interface may include at least one hook member that is configured to engage and retain an edge portion of the cartridge.

In some embodiments, the cartridge holding interface is configured to interface with the cartridge in a single orientation.

In some embodiments, at least one chamber includes a plurality of chambers and the at least one aperture includes a plurality of apertures. The base housing member and the cover housing member include cooperating sealing members that are configured to seal each of the plurality of chambers. In some embodiments, the cooperating sealing members include a base sealing feature between the plurality of wells on the base housing member, and a cover sealing feature on the cover housing member configured to engage with the base sealing feature and to thereby fluidly seal each of the plurality of wells. One of the base sealing feature and the cover sealing feature may include a groove and the other of the base sealing feature and the cover sealing feature comprises a ridge that is configured to be received in the groove and form a snug fit. In some embodiments, the chambers overlap a central portion and a perimeter portion of the base housing member, and the chambers comprise a wall that has a height that is higher in the central portion than at the perimeter portion.

In some embodiments, a collection and transfer assembly includes a collection device. The collection device includes a base housing member having at least one chamber, and a cover housing member having at least one housing aperture therein. The cover housing member is configured to cover the base housing member such that the at least one housing aperture is positioned in fluid communication with the at least one chamber. The cover housing member further includes a cartridge holding interface. The collection and transfer assembly further includes a sample cartridge comprising at least one sample area having at least one cartridge aperture that is configured to receive a fluid from the at least one chamber via the at least one housing aperture. The cartridge holding interface on the cover housing member is configured to releasably engage with the sample cartridge.

In some embodiments, the sample cartridge has a first major surface opposite a second major surface, the at least one sample area is on the first major surface and faces away from the cover housing member, and the at least one cartridge aperture is on the second major surface and fluidly connects the housing aperture to the sample area. In some embodiments, the sample cartridge has a first major surface opposite a second major surface, and the at least one sample area is on the second major surface and faces toward the cover housing member, and the at least one cartridge aperture is on the second major surface and fluidly connects the housing aperture to the sample area.

In some embodiments, the cartridge holding interface comprises a retaining wall or protruding pins or posts configured to abut an outer perimeter of the cartridge. The cartridge holding interface may include at least one notch and/or groove that is configured to engage a corresponding notch and/or groove on the cartridge. The cartridge holding interface may include at least one hook member that is configured to engage and retain an edge portion of the cartridge.

In some embodiments, the cartridge holding interface is configured to interface with the cartridge in a single orientation.

In some embodiments, the at least one chamber includes a plurality of chambers and the at least one aperture includes a plurality of apertures. The base housing member and the cover housing member may include cooperating sealing members that are configured to seal each of the plurality of chambers. In some embodiments, the cooperating sealing members include a base sealing feature between the plurality of wells on the base housing member, and a cover sealing feature on the cover housing member configured to engage with the base sealing feature and to thereby fluidly seal each of the plurality of wells. One of the base sealing feature and the cover sealing feature may include a groove and the other of the base sealing feature and the cover sealing feature may include a ridge that is configured to be received in the groove and form a snug fit. In some embodiments, the chambers overlap a central portion and a perimeter portion of the base housing member, and the chambers include a wall that has a height that is higher in the central portion than at the perimeter portion.

In some embodiments, a method of collecting a sample includes collecting a sample in at least one chamber of a base housing member of a collection device. A cover housing member is placed on the base housing member of the collection device. The cover housing member has at least one housing aperture therein. The cover housing member is configured to cover the base housing member such that the at least one housing aperture is positioned in fluid communication with the at least one chamber. The cover housing member further includes a cartridge holding interface. A sample cartridge is positioned on the cartridge holding interface. The sample cartridge further includes at least one sample area having at least one cartridge aperture that is configured to receive a fluid from the at least one chamber via the at least one housing aperture. The cover and base housing members are inverted such that the sample flows from the at least one chamber to the at least one sample area via the at least one housing aperture and the at least one cartridge aperture.

In some embodiments, the method further includes placing the cartridge in an imaging reader.

In some embodiments, the method further includes storing the collection device and the sample cartridge before the inverting step.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
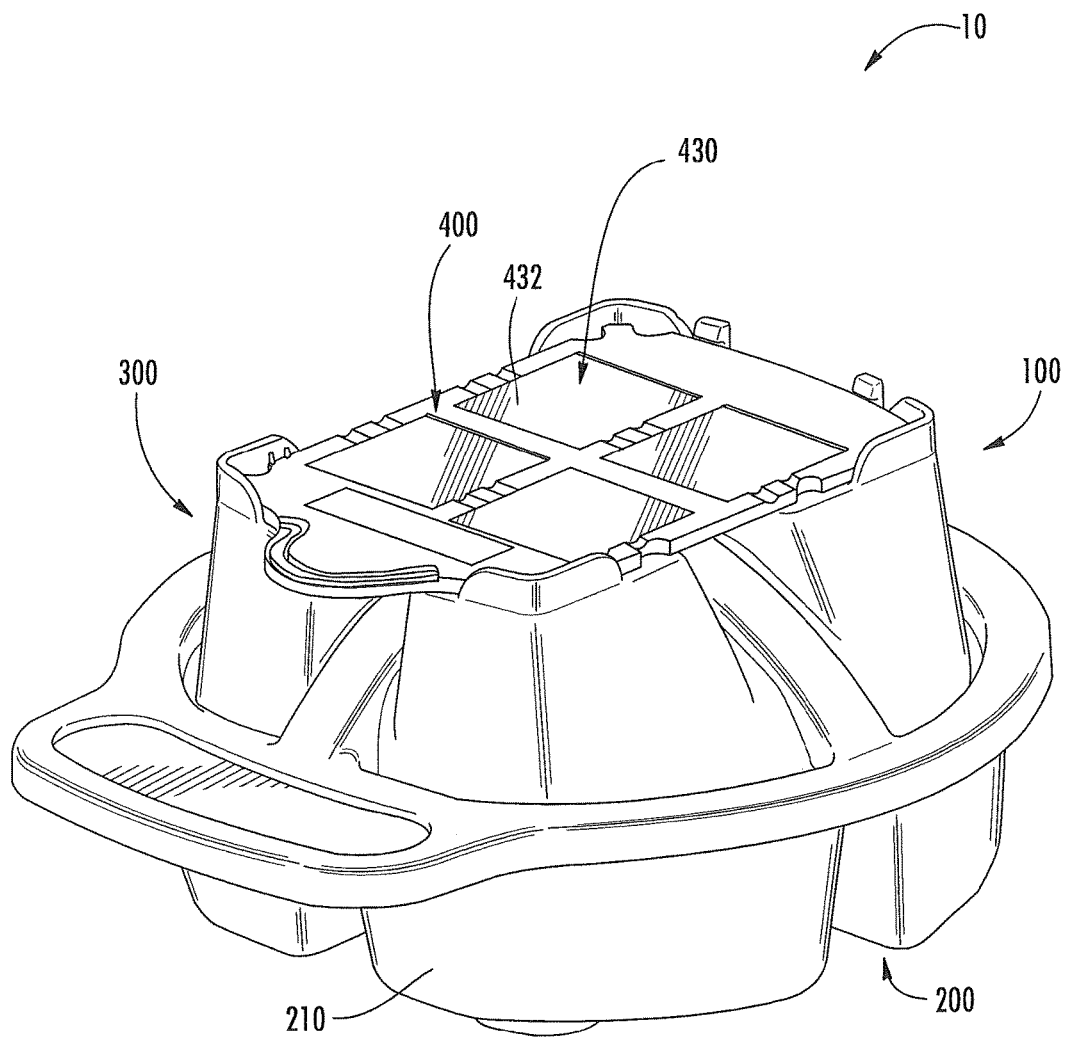
FIG. 1 is a front perspective view of a collection and transfer device with a sample cartridge according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc., may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

Figure 2:
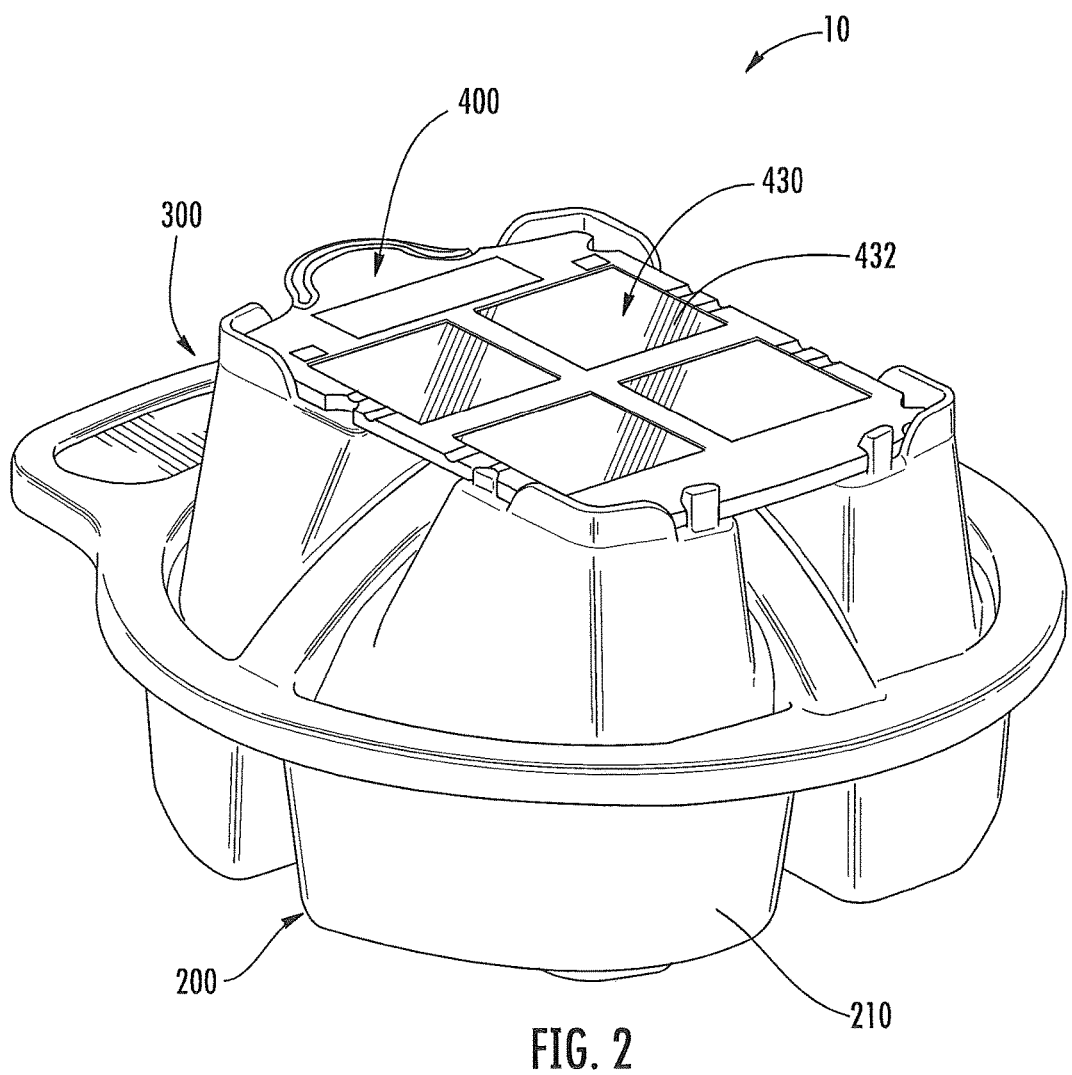
FIG. 2 is a back perspective view of the collection and transfer device of FIG. 1.
Figure 3:
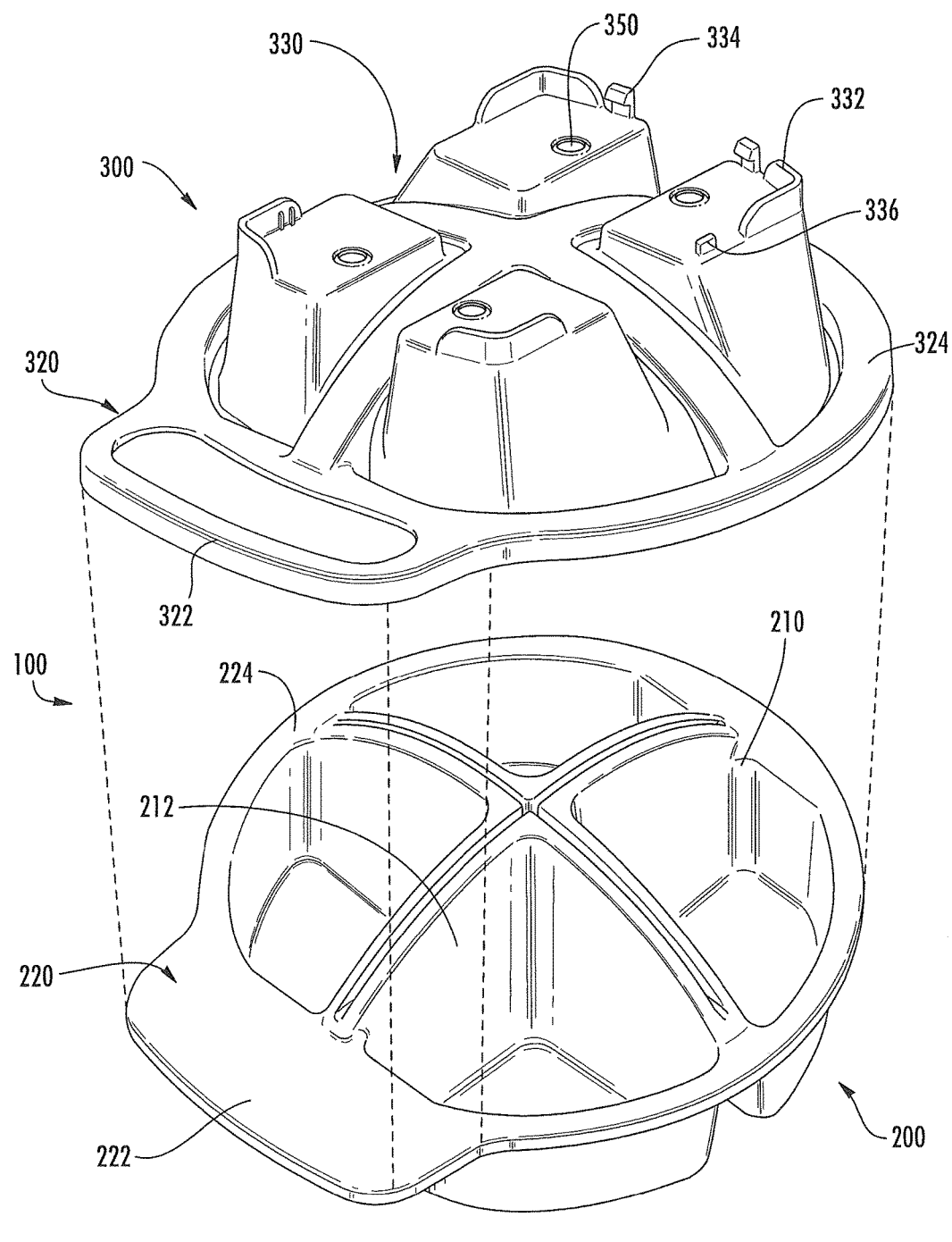
FIG. 3 is a front perspective view of a base housing and a cover housing of the collection and transfer device of FIG. 1 in an open configuration.

Embodiments according to the present invention will now be described with respect to FIGS. 1-24. As illustrated in FIGS. 1-2, a collection and transfer assembly 10 includes a collection device 100 and a sample cartridge 400. The collection device 100 includes a base housing 200 and cover housing 300. The base housing 200 includes four chambers 210 that are configured to collect a sample. The sample cartridge 400 includes four sample areas 430, which are configured to receive the sample from the chambers 210 for further analysis. In some embodiments, the collection and transfer assembly 10 may be used to collect a liquid biological fluid sample, for example, a milk sample from a milk producing animal, such as a cow or goat. Accordingly, the milk sample may be conveniently collected and transferred to the microscope slide for further analysis, for example, in a microscope or imaging reader. The sample areas 430 may include a wedge-shaped microscope slide such that capillary action fills the slide 430 with the sample as a "self-preparing wet smear" with a meta-chromatic stain. The stain may be preloaded onto the sample areas 430. The wedge-shaped microscope slide with the stained sample may be analyzed by visual identification and direct observation or by imaging instruments using computer-enhanced digital camera images. Examples of suitable imaging readers and wedge-shaped slides are described in U.S. Patent Application Publication No. 2009/0233329 to Rodriguez. The cartridge for imaging a specimen on an automated microscope may include a substrate, a chamber or generally planar imaging surface on or in the substrate for containing or supporting the specimen; a plurality of exogeneous targets in the chamber or on the surface; and (optionally but in some embodiments preferably) at least one optically transparent wall formed on or forming the chamber to facilitate imaging the contents thereof.

As illustrated in FIGS. 3-7, the base housing 200 defines four chambers 210 having centrally elevated splash-guard walls 212, a groove 214, and an outer lip 220 that includes a handle portion 222 and a perimeter portion 224. The cover housing 300 includes a plurality of apertures 316, an outer lip 320 includes a handle portion 322 and a perimeter portion 324. The cover housing 300 further defines a cartridge holding interface 330 that is sized and configured to releasably engage with and/or abut the cartridge 400 (FIGS. 1-2). As shown, for example, in FIG. 3, the cartridge holding interface 330 includes various retaining features, including retaining walls 332, retaining members or hooks 334, and interlocking member or notch 336, and retaining pins 338.

Figure 4:
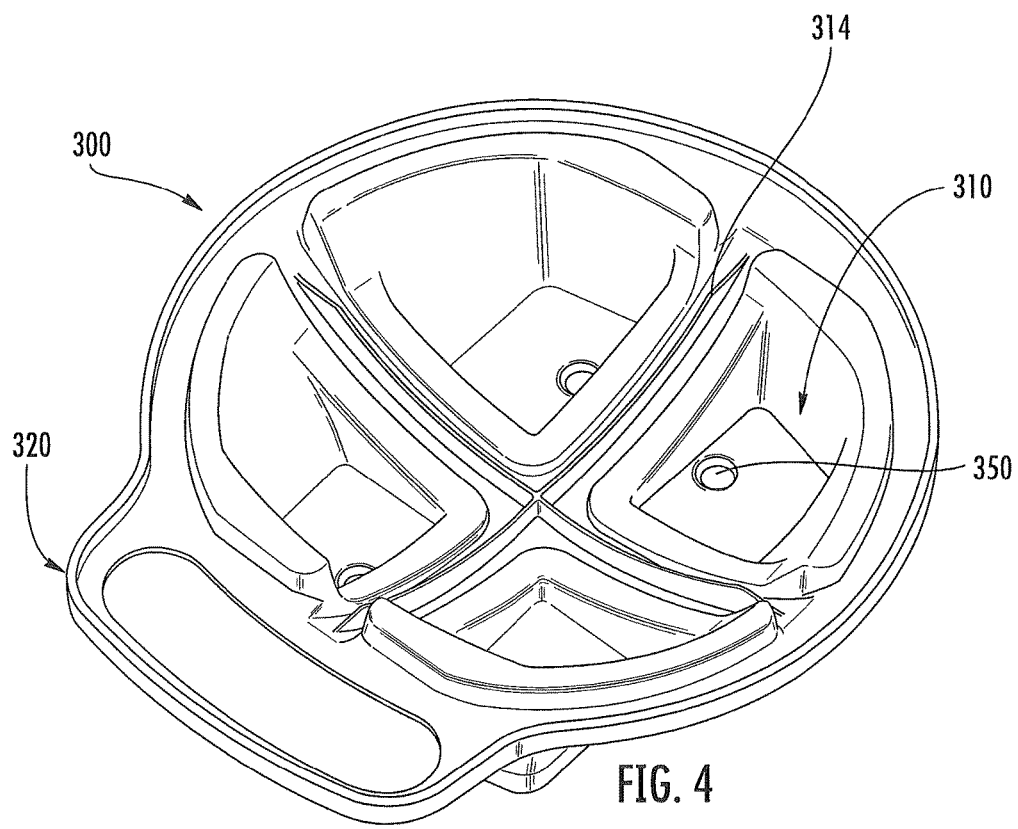
FIG. 4 is an interior perspective view of the cover housing of the collection and transfer device of FIG. 1.
Figure 5:
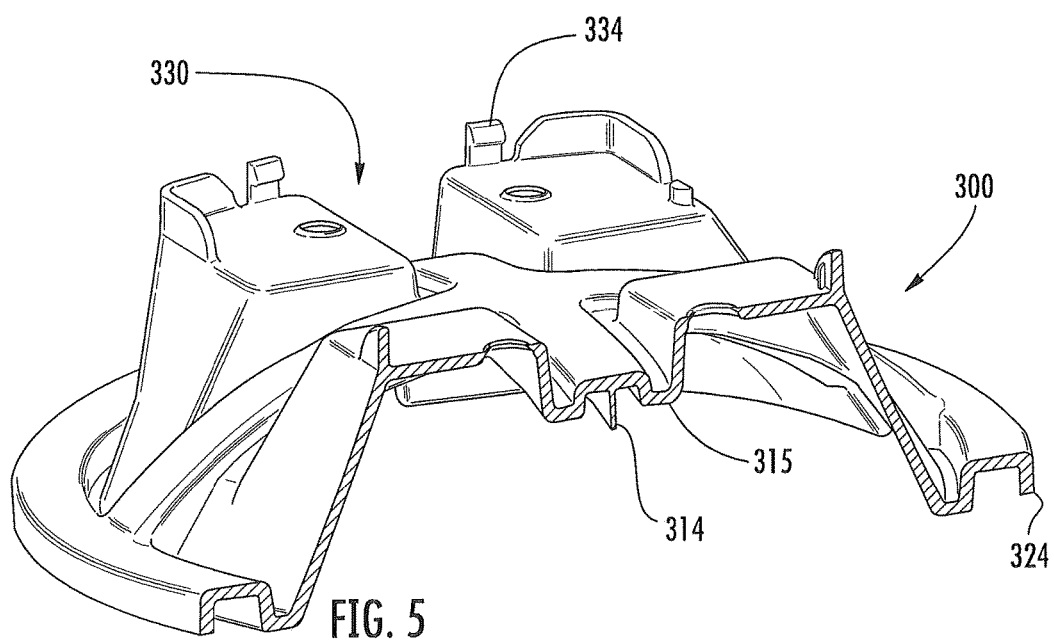
FIG. 5 is a cross-sectional perspective view of the cover housing of the collection and transfer device of FIG. 1.
Figure 6:
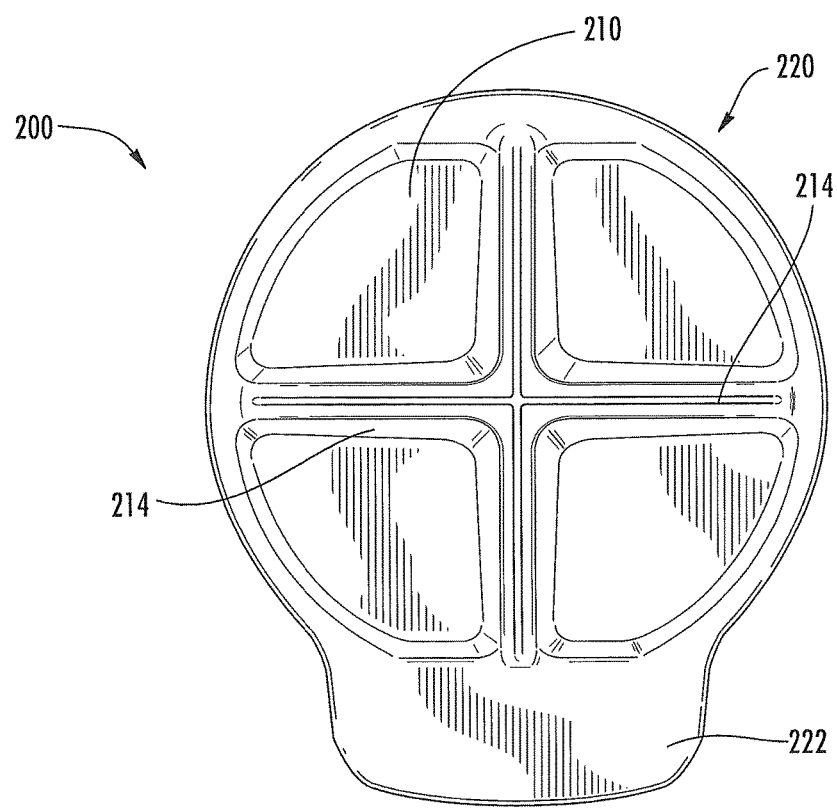
FIG. 6 is a top view of the base housing of the collection and transfer device of FIG. 1.
Figure 7:
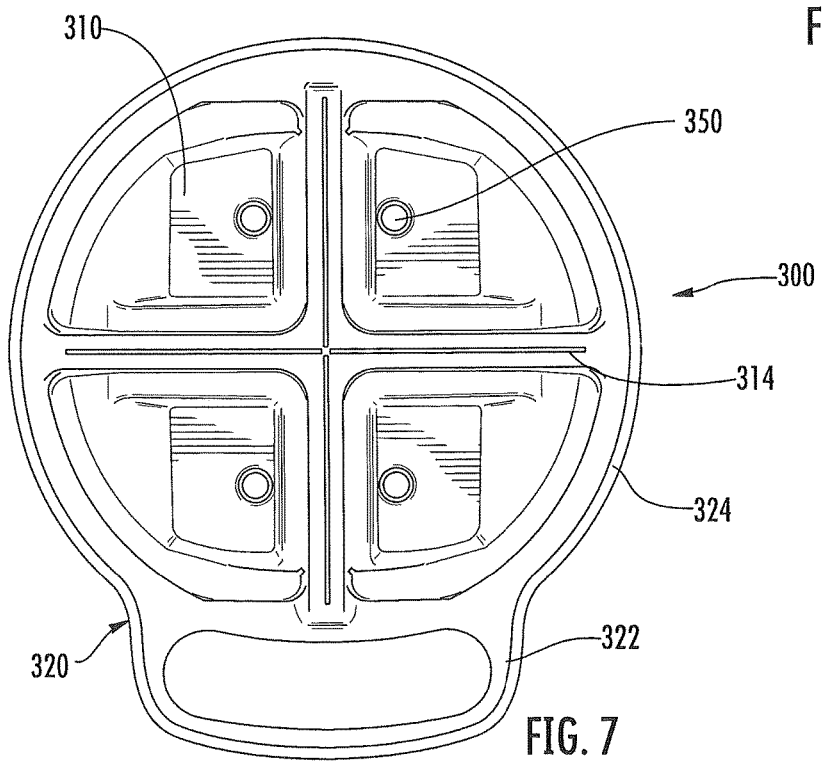
FIG. 7 is a top view of the cover housing of the collection and transfer of FIG. 1.

As illustrated, for example, in FIG. 4, the cover housing 300 includes chamber covering sealing 310 that correspond to the chambers 210 of the base housing 200. The chamber sealing features 310 are configured to seal and/or fluidly isolate different samples that are collected in each of the four chambers 210 of the base housing 200. As illustrated, the chamber sealing features 310 include a sealing rib 314 on a ridge interface 315, and sealing protrusions 318. The sealing rib 314 is configured to mate with the groove 214 of the base housing 200, and the sealing protrusions 318 are configured to extend into the chambers 210 of the base housing 200 such that a fluid sample in each of the chambers 210 is generally prevented from leaking into other ones of the chambers 210.

Figure 10:
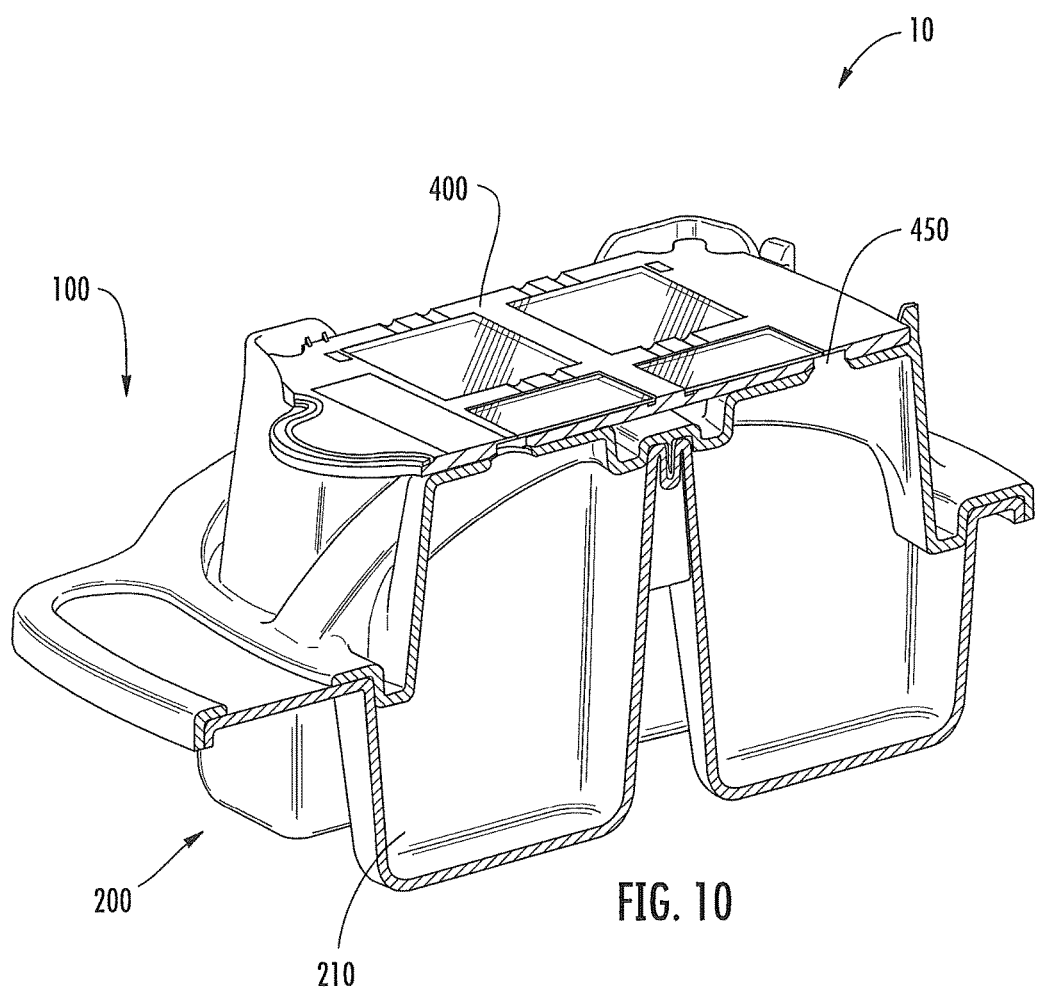
FIG. 10 is a cross-sectional perspective view of the collection and transfer device and the cartridge of FIG. 1.

In this configuration, and as illustrated in FIG. 10, the base housing 200 and the cover housing 300 interlock with on another to generally seal each of the sample chambers 210 to reduce or prevent leaking between chambers 210. Therefore, the samples from the quadrants of the cow may be separately stored and/or tested separately. In particular, the lips 220, 320 may engage with one another (such as in a snap- or press-fit) to form an outer seal. The sealing protrusions 318 of the cover housing 300 extend into the chambers 210 to further seal the sample chambers 210. The sealing rib 314 and ridge interface 315 of the cover housing 300 mate with the central groove 214 of the base housing 200 to form a sufficiently snug fit to generally seal the four chambers 210 and/or reduce or prevent sample fluid from one chamber 210 leaking to another chamber 210.

Figure 8:
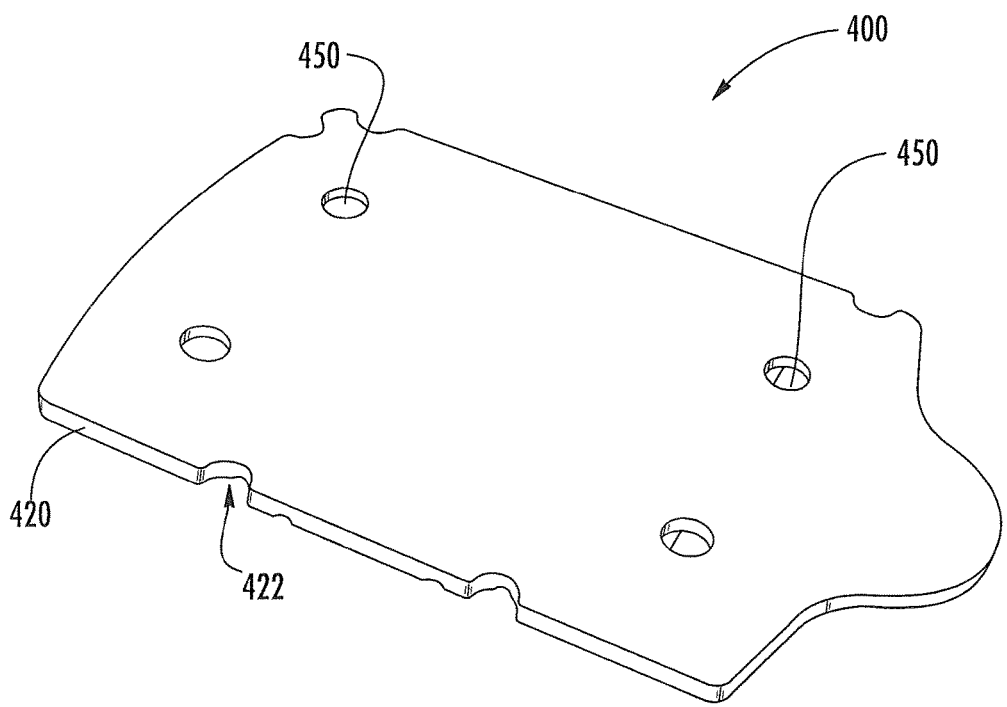
FIG. 8 is a bottom perspective view of the cartridge device of FIG. 1.
Figure 9:
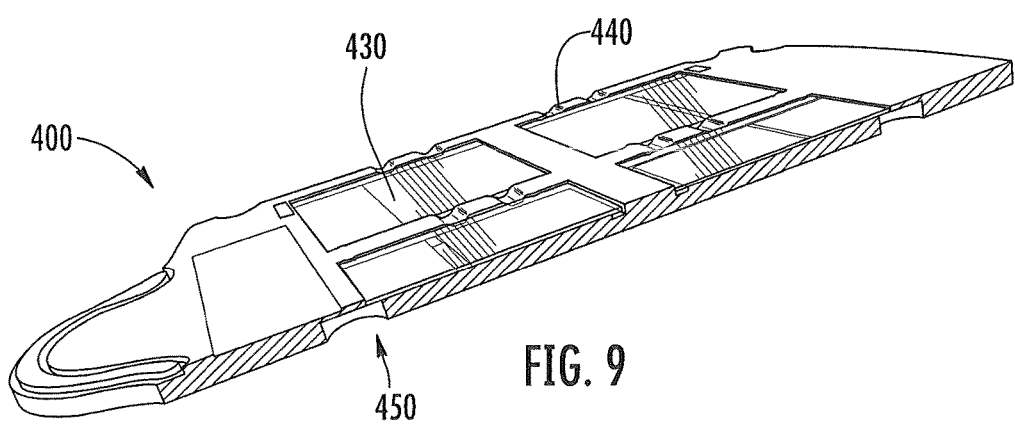
FIG. 9 is a cross-sectional top perspective view of the cartridge device of FIG. 1.

As shown in FIGS. 8-9, the sample cartridge 400 includes an outer perimeter 420, sample areas 430, and apertures 450. The outer perimeter 420 has an asymmetric shape and orientation features, such as notches 422, for interacting with the cartridge holding interface 330 of the collection device cover housing 300. The sample areas 430 include a transparent or translucent slide 432, such as a microscope slide, that is configured to hold and retain the fluid sample for analysis by a slide reader (not shown). The apertures 450 are sized and configured to provide a fluid connection with the apertures 350 of the cover housing 300.

Figure 11:
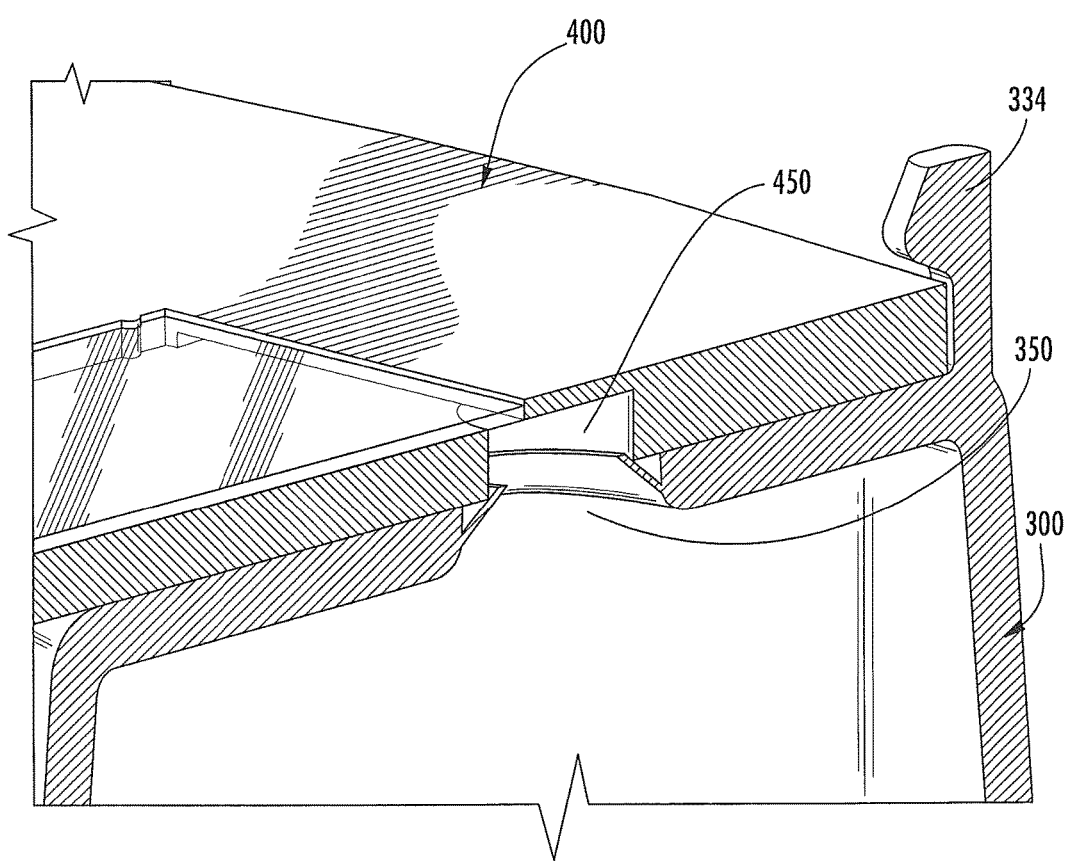
FIG. 11 is an exploded cross-sectional perspective view of the collection and transfer device interface with the cartridge device of FIG. 1.
Figure 12:
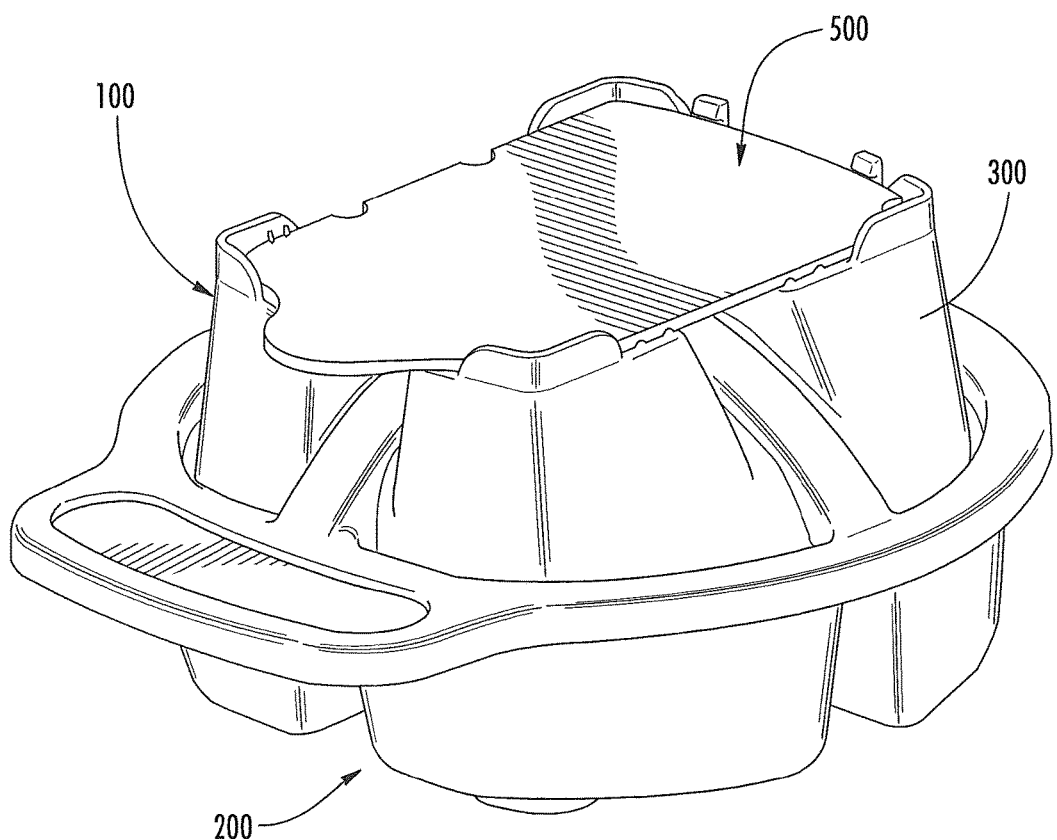
FIG. 12 is a perspective view of a collection and transfer device and a sample cartridge device according to some embodiments.
Figure 13:
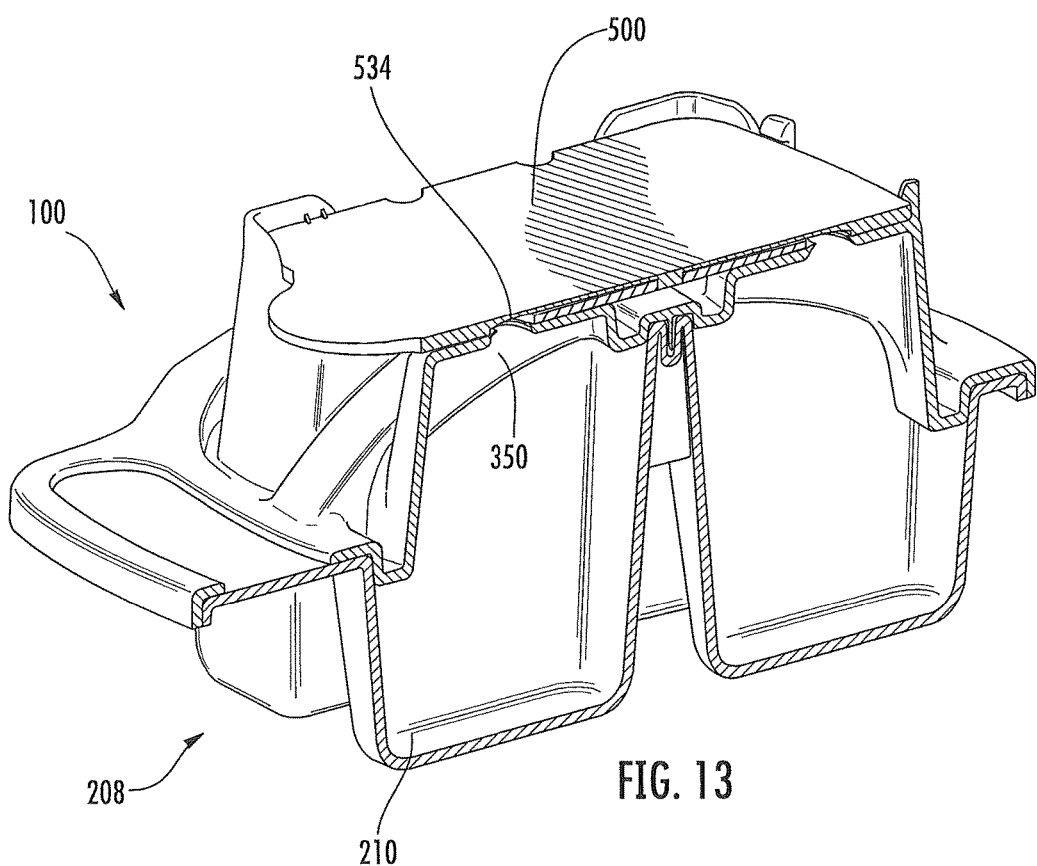
FIG. 13 is a cross-sectional perspective view of the collection and transfer device of FIG. 12.
Figure 14:
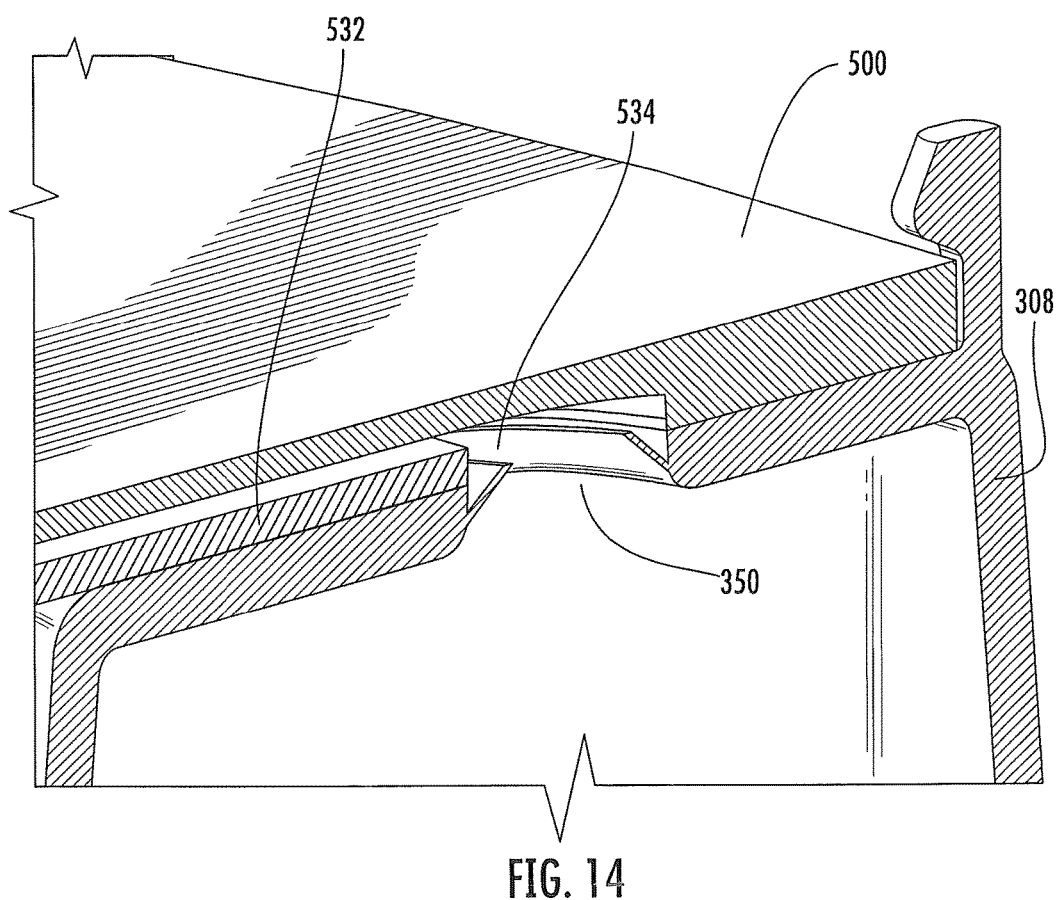
FIG. 14 is an exploded cross-cross sectional perspective view of the collection and transfer device interface with the cartridge device of FIG. 12.

As illustrated in FIGS. 10-11, a fluid sample collected in the chambers 210 may be transferred to the sample areas 430 of the sample cartridge 400 by inverting the collection and transfer chamber 10. In an inverted position, the fluid sample flows from the base chamber 210 to the cover housing 300 and into the sample area 430 via the cover housing apertures 350 and the sample cartridge apertures 450.

Accordingly, corresponding interlocking features, such as notches and/or grooves 336 and 422 may be included in the outer perimeter 420 of the cartridge 400. In addition, the cartridge holding interface 330 and the outer perimeter 420 of the cartridge 400 may be asymmetric such that the cartridge 400 fits into the cartridge holding interface 330 in only a single orientation. Moreover, the hooks 334 may further hold the cartridge 400 in position such that the assembly 10 may be inverted or transported without the cartridge 400 becoming dislodged from the cartridge holding interface 330.

Embodiments according to the invention are described above with respect to a configuration in which the fluid enters the cartridge 400 via the bottom (or the major side opposite the sample areas 430) such that a user may view the sample in the sample areas 430 when the cartridge 400 is in position on the cover housing 300. It should be understood, however, that other configurations may be used to provide a fluid pathway from the sample chambers 210 to a sample region, such as on a microscope slide. For example, as illustrated FIGS. 12-14, a sample cartridge 500 includes an outer perimeter 520, sample areas 530, and apertures 550. The sample areas 530 include a transparent or translucent slide 532 and sample entry passages 534. The slide 532 may be a microscope slide that is configured to hold and retain the fluid sample for analysis by a slide reader (not shown). The entry passages 534 are positioned so as to provide a fluid passageway from the apertures 350 of the cover housing 300. Accordingly, when the device 100 is inverted, the sample flows from the chambers 210 to the sample areas 530 via the apertures 350 and the passages 534. As illustrated, the slide 532 is on a side of the cartridge 500 that faces the collection device cover housing 300.

In a similar manner as described above with respect to the cartridge 400, the outer perimeter 520 of the cartridge 500 has an asymmetric shape and orientation features, such as notches 522, for interacting with the cartridge holding interface 330 of the collection device cover housing 300. Therefore, the cartridges 400, 500 may be configured to mate with the cartridge holding interface 330 in a single orientation. In this configuration, the sample may be collected in the chambers 210 corresponding to predefined quadrant of the cow or other sample source. The cartridges 400, 500 may be configured to fit on the holding interface 330 in a single orientation so that the source of the sample from one of the predefined quadrants is known. The cartridges 400, 500 may also fit into a reader (not shown) in a single orientation so that the reader associates the sample results with a predefined quadrant of the cow or other sample source. The sample results may be recorded by a user or by a computer processor associate with the reader. The sample results may be recorded together with the sample source, such as a cow identification number and a quadrant number based on the particular chamber 210 and corresponding sample area 430, 530.

Figure 15:
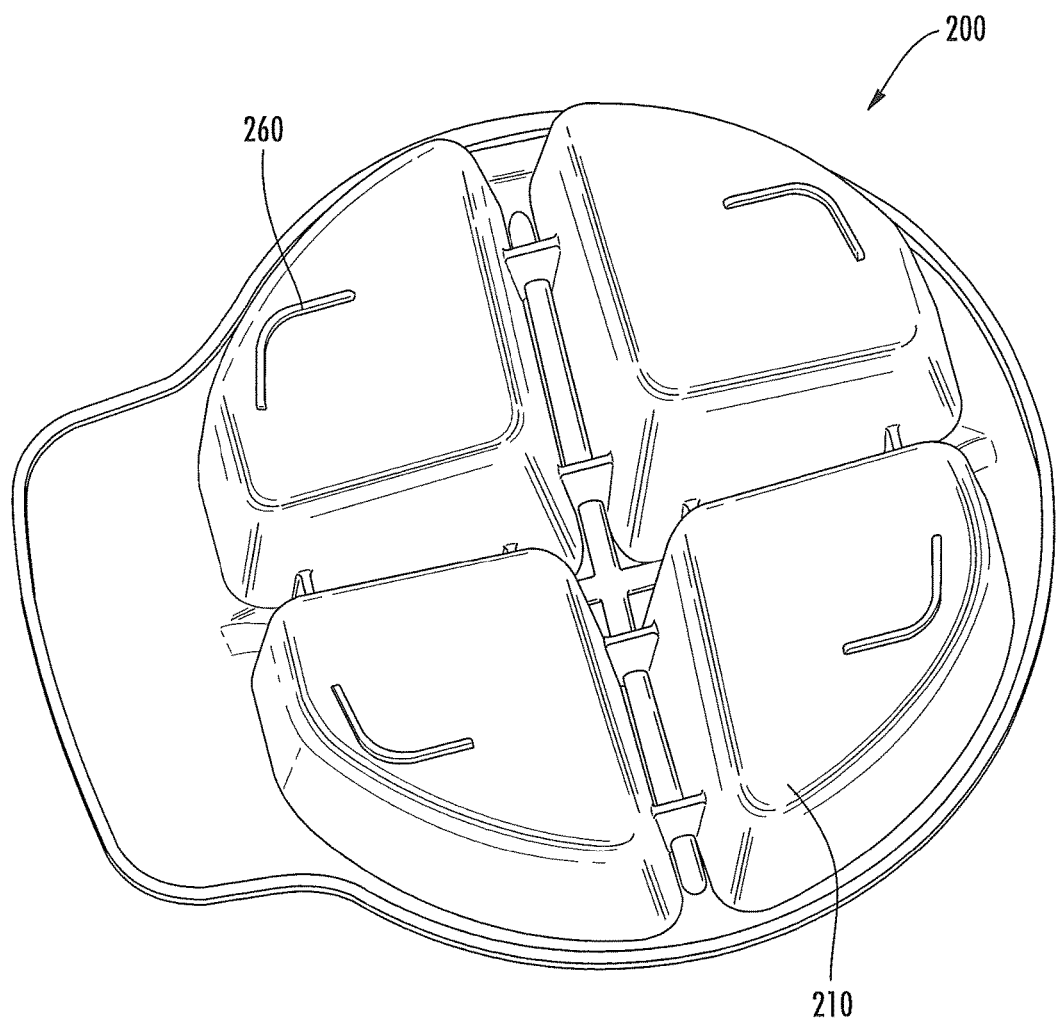
FIG. 15 is a bottom perspective view of the collection and transfer device base housing of FIG. 1.
Figure 16:
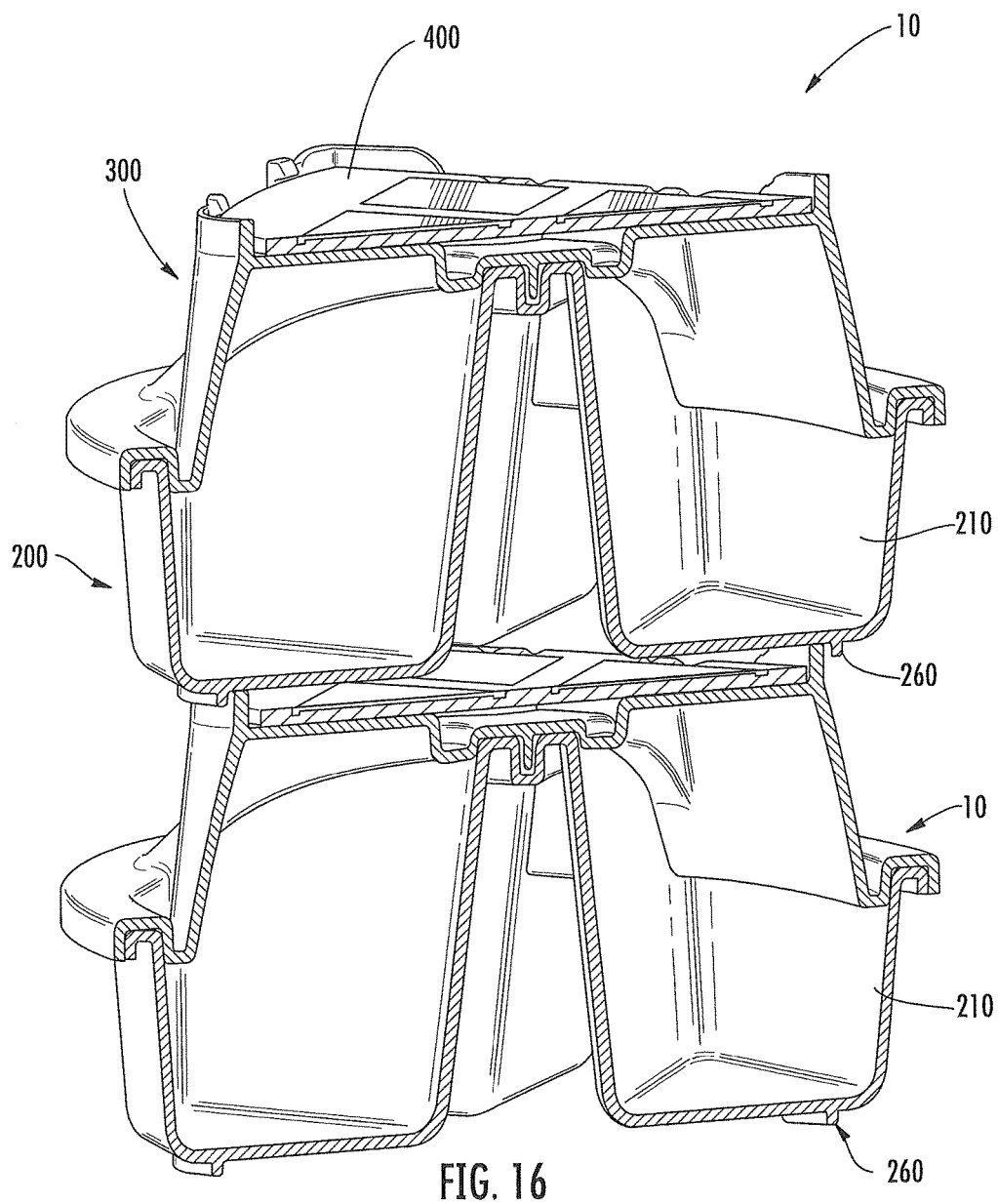
FIG. 16 is a cross-sectional perspective side view of two collection and transfer devices with corresponding sample cartridges in a nesting configuration according to some embodiments.

As shown in FIG. 15, the base housing 200 may include nesting features 260 that generally correspond to the cartridge holding interface 330 or other top features of the cover housing 300. As illustrated in FIG. 16, the nesting features 260 permit the stacking of two or more collection and transfer assemblies 10 by resting the nesting features 260 against the cartridge holding interface 330 of an adjacent assembly 10. As shown in FIG. 16, the cartridge holding interface 330 is shaped such that it fits inside the nesting features 260 of an adjacent assembly 10. In some embodiments, the collection devices 100 may be filled with fluid samples, and then stored in the stacked configuration. The fluid samples may be collected in the sample chambers 210 without being added to the cartridges 400 during storage. Accordingly, contact between the fluid sample and the assay and/or stain in the sample area 430 may be avoided until just prior to analyzing the sample in the cartridge 400 when the collection and transfer assembly 10 may be agitated and inverted to thereby cause fluid to flow from the chamber 210 to the sample area 430 via the cover apertures 350 and the cartridge apertures 450. Therefore, the user may collect samples from multiple bovine animals prior to analysis and store the samples without contacting the sample with the assay and/or stain in the sample area 430 until the user chooses to analyze the cartridges 400.

Figure 17:
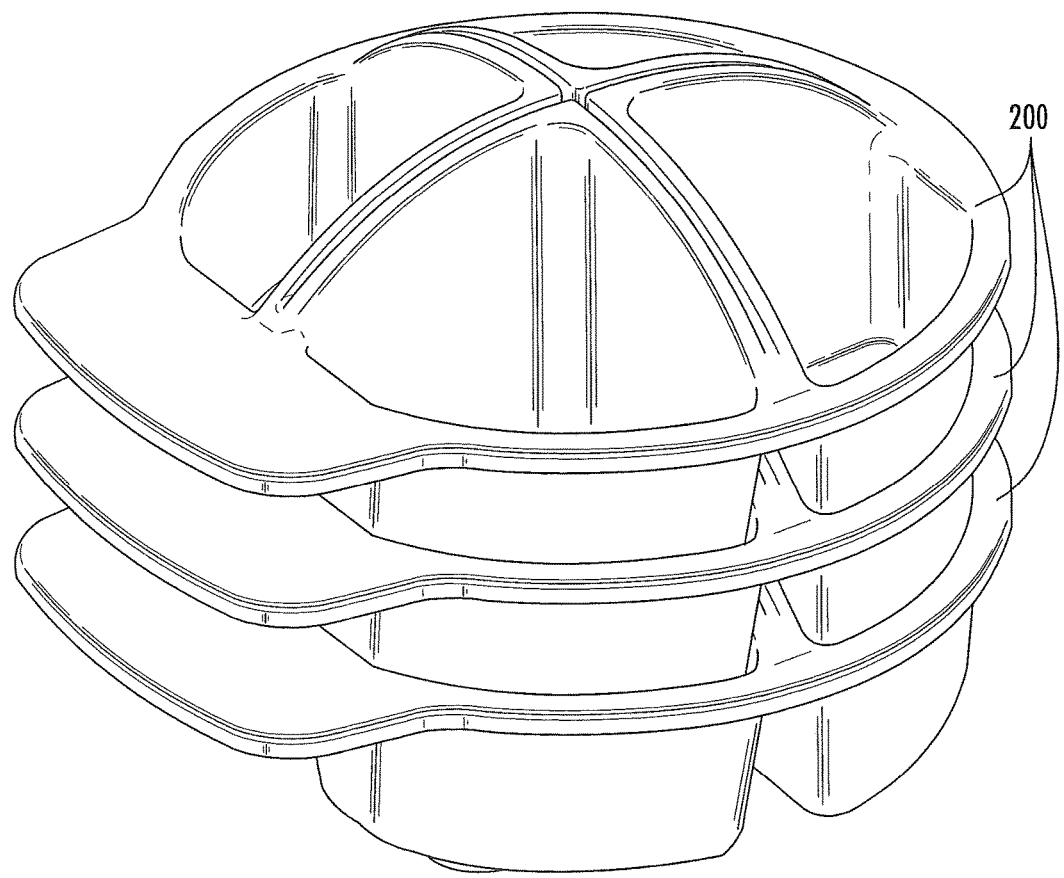
FIG. 17 is a perspective side view of a plurality of the base housings of collection and transfer devices in a nesting configuration according to some embodiments.

The chambers 210 of the base housing 200 may be tapered to permit nesting of the sample collection base housing 200 for ease of transport and/or shipping as illustrated in FIG. 17.

Figure 18:
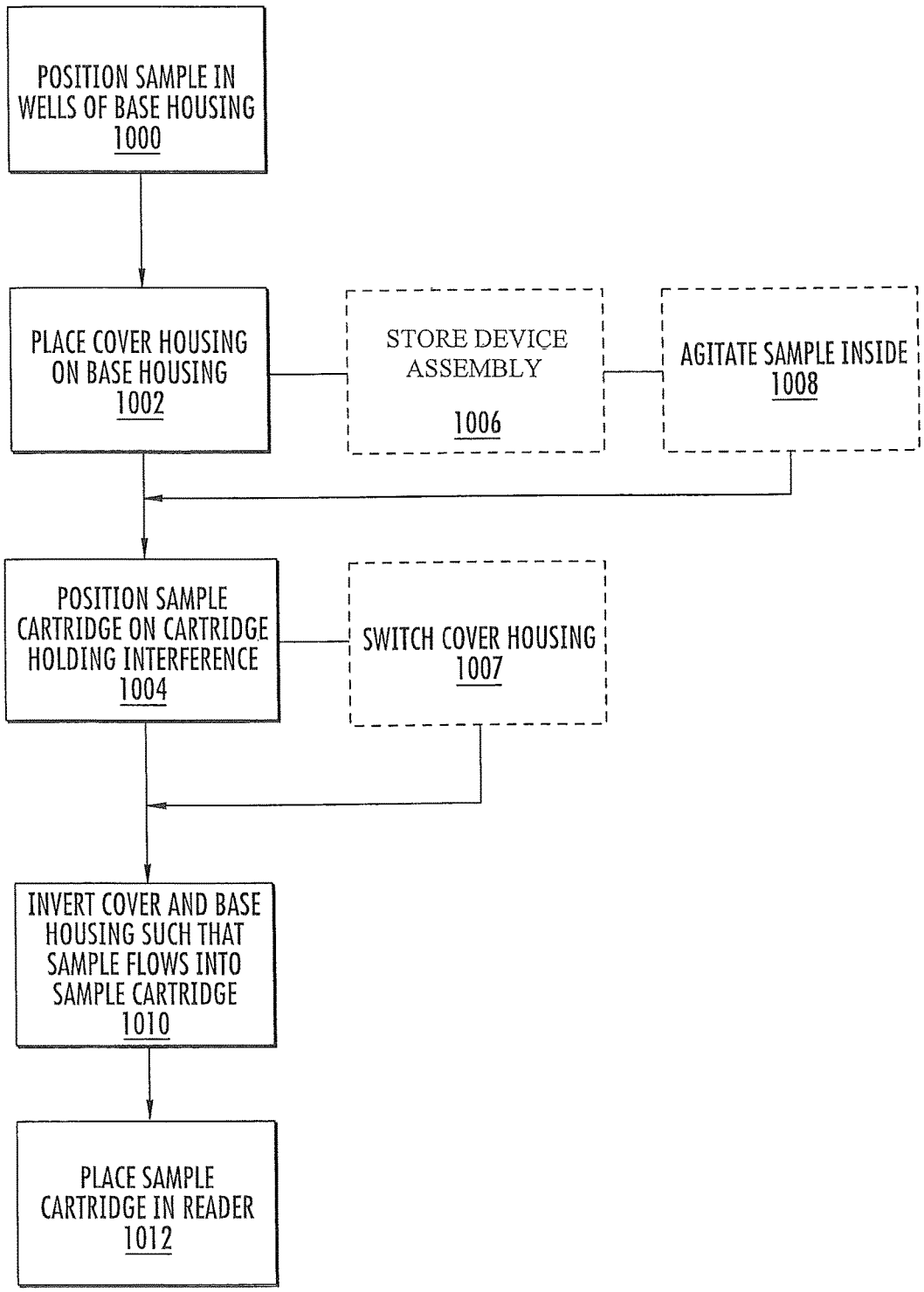
FIG. 18 is a flowchart illustrating operations according to some embodiments.

Operations according to some embodiments are shown in FIG. 18. A fluid sample, for example, milk from a cow, goat or other milk producing animal, may be collected in the chambers of the base housing (Block 1000; FIG. 18). As shown in FIGS. 1-7 and 10, the chambers 210 of the base housing 200 include splash-guard walls 212 that are sufficiently high that splatter may be reduced between the chambers 210. Fluid milk samples may be collected directly from each of the four quadrants or teats of the cow generally without mixing samples collected from other quadrants of the milk-producing animal due, in part, to the high splash-guard walls 212. The cover housing may then be placed on the base housing (Block 1002; FIG. 18). In some embodiments, however, the cover housing may be a temporary plug housing, such as the housing 1500 of FIG. 25 that is placed on the base housing 1200 for storage, transportation and/or agitation of the sample. The device assembly may be stored (Block 1006). In some embodiments, the assembly may be stored prior to analysis and/or filing the cartridge sample areas. However, in some embodiments, the sample areas of the cartridge may be filed with the fluid sample prior to storage. Before the sample cartridge is filled, the plug (if used) is replaced with the transfer cover and the sample cartridge is positioned on the cartridge holding interface of the cover housing.

When the user wishes to initiate sample analysis, the sample may be agitated, for example, in the base housing, because fluids such as milk may separate into high- and low-fat components (Block 1008). If the cover housing 1500 of FIG. 25 was used, then the cover housing 1500 is first replaced with the cover housing 1200 and cartridge 1400 (Block 1007). The cover and the base housing may be inverted such that the sample flows into the cartridge sample areas via the cover housing apertures and the cartridge apertures (Block 1010). The sample cartridge may then be removed from the cover housing and placed in a reader (Block 1012) for further analysis.

Although embodiments according to the present invention are described herein with respect to four sample areas 430 and corresponding cartridge filling apertures 450, cover housing filling apertures 350, and collection chambers 210, it should be understood that any number of sample areas 430 may be provided. In some embodiments, a single sample area may be used with corresponding filling apertures and a single collection chamber.

Figure 19:
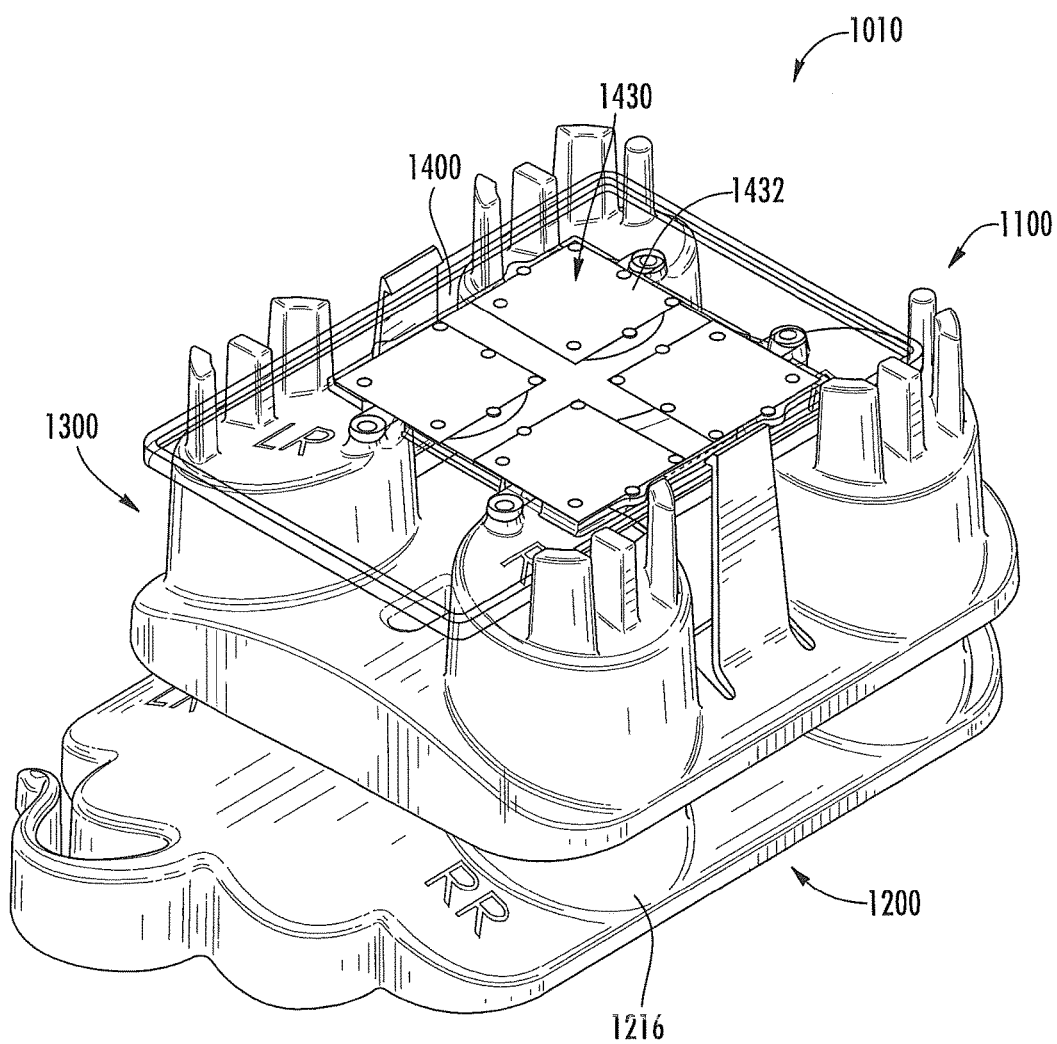
FIG. 19 is a front perspective view of a collection and transfer device with a sample cartridge according to some embodiments.

As illustrated in FIG. 19, a collection and transfer assembly 1010 includes a collection device 1100 and a sample cartridge 1400. The collection device 1100 includes a base housing 1200 and a cover housing 1300. The base housing 1200 includes four generally cylindrical chambers 1210 and on a base or main portion 1220. The chambers 1210 include a wall portion that extends away from the main portion 1220 and into corresponding, cooperating cover sealing features 1310 on the cover housing 1300. The sealing features 1310 cover the chambers 1210 and may form a tight fit to substantially isolate and reduce or prevent leakage from the chambers 1210. The cover housing sealing features 1310 further include apertures 1350. The sample cartridge 1400 includes sample areas 1430, which are defined by sample slides 1432. The sample areas 1430 include apertures 1452 that cooperate with the apertures 1350 of the cover housing 1300. In this configuration, a milk sample may be collected in the chambers 1210 of the base housing 1200 and sealed by the cover housing 1300. The milk sample may be received in the sample areas 1430 of the sample cartridge 1400 when the assembly 1010 is inverted, and the milk sample flows from the chambers 1210 via the apertures 1350 and 1452 and into the sample area 1430.

Figure 20:
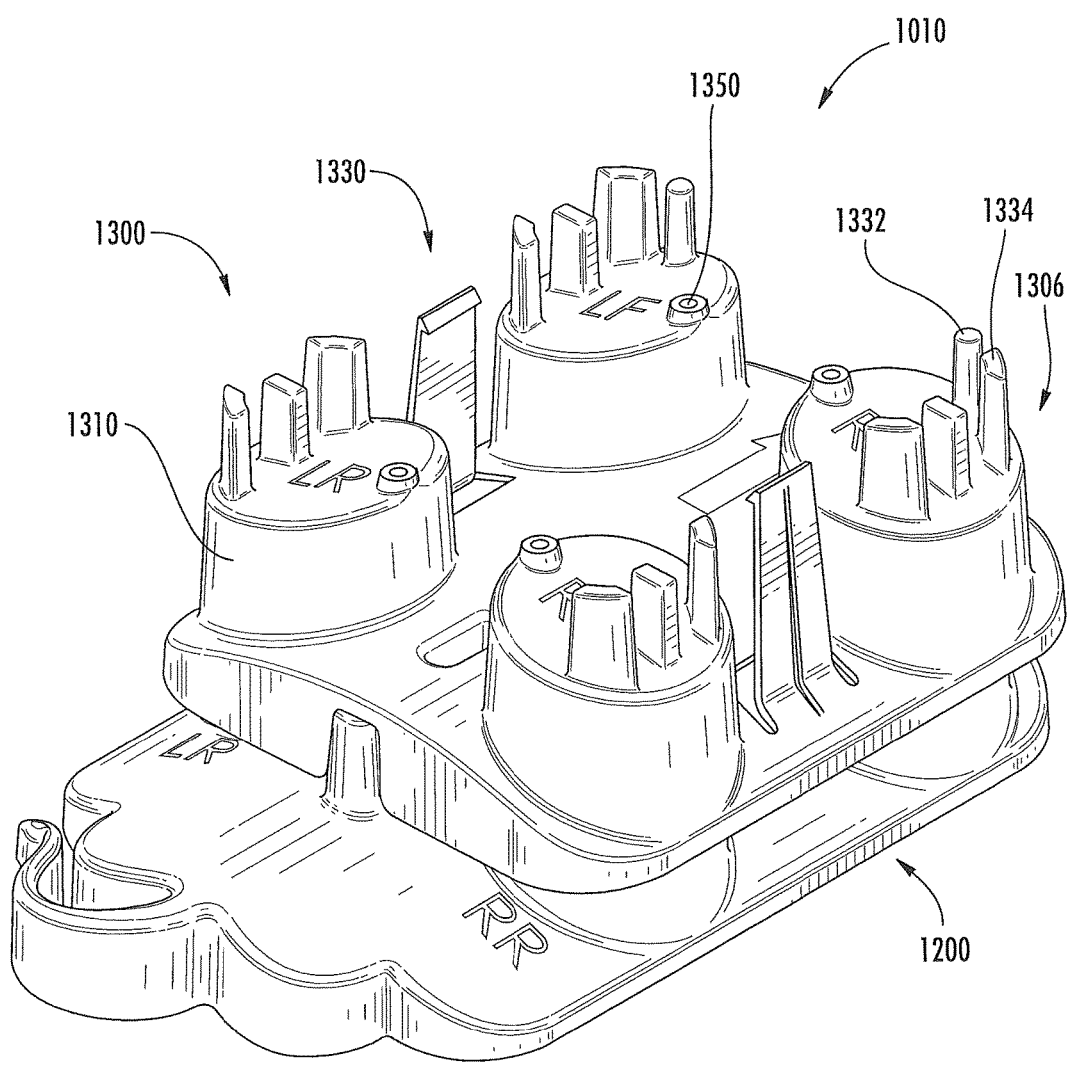
FIG. 20 is a front perspective view of a collection and transfer device with the sample cartridge removed according to some embodiments.
Figure 21:
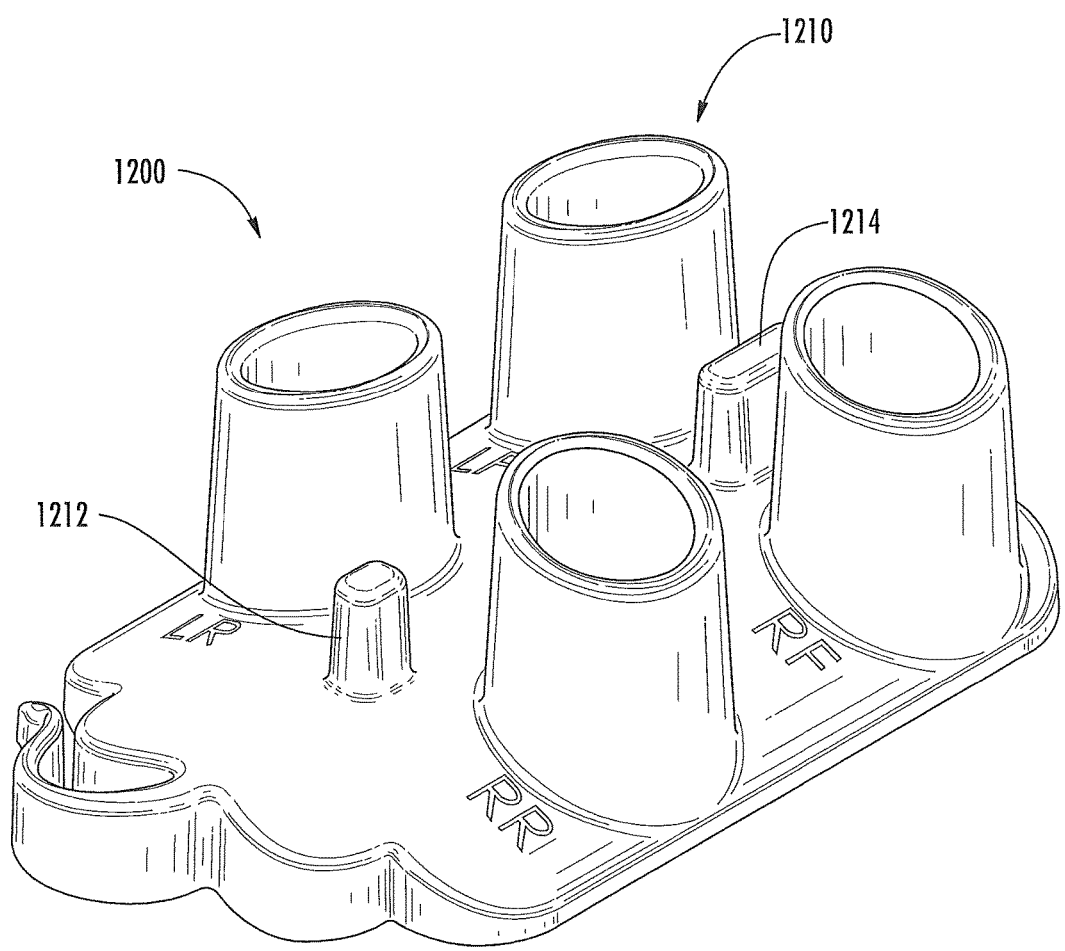
FIG. 21 is a front perspective view of the base housing of the collection and transfer device of FIG. 20.

As illustrated in FIG. 20, the cover housing 1300 includes a holding interface 1330 having various retaining features 1332, 1334 and 1336 for retaining the sample cartridge 1400. In some embodiments, the retaining features 1332, 1334 and 1336 may be assymetric such that the cartridge 1400 fits into the interface 1330 in a single orientation. As shown in FIG. 21, the chambers 1210 of the base housing 1200 are illustrated in additional detail. As illustrated, the chambers 1210 include asymmetric or angled walls that may reduce splashing or contamination from one chamber to another because the wall height of the chambers 1210 is greater toward the central region of the base housing 1200.

Figure 22:
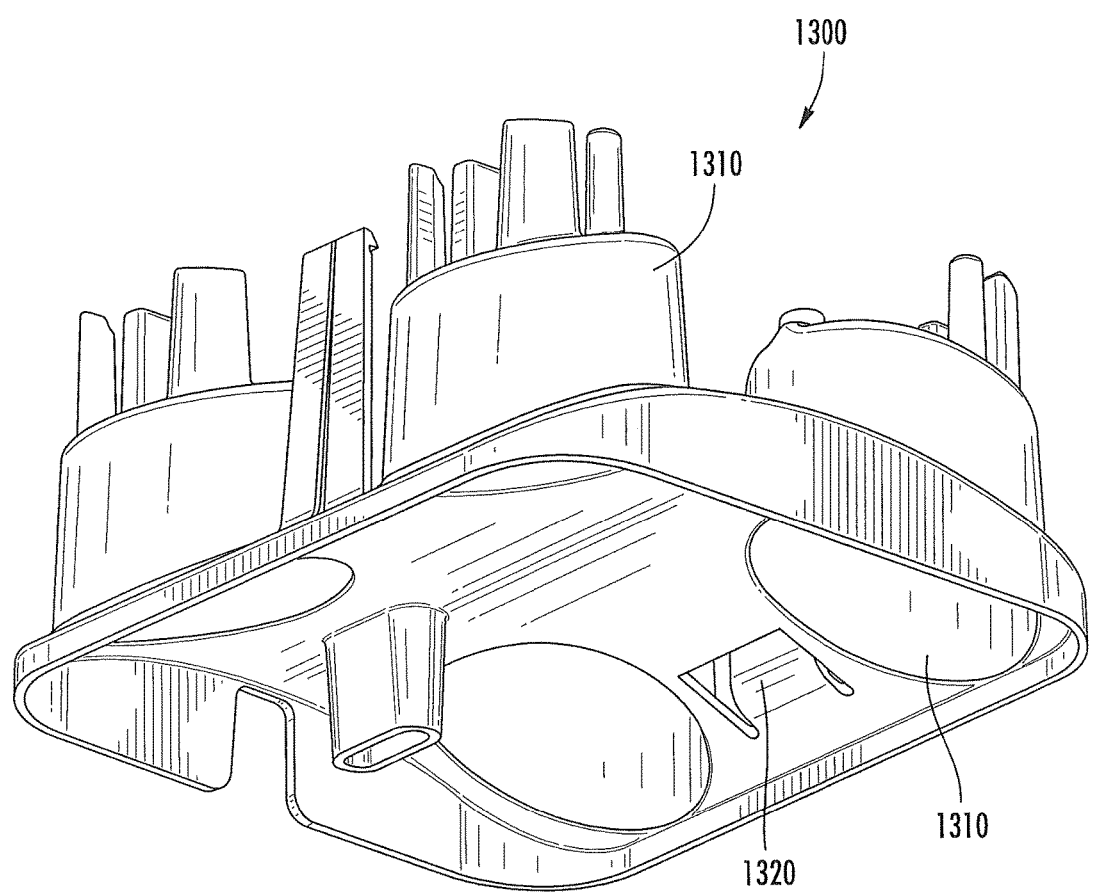
FIG. 22 is a bottom perspective view of the cover housing of the collection and transfer device of FIG. 20.

In some embodiments, the base housing 1200 and the cover housing 1300 may include various features that interact for stability of assembly and/or so that the base housing 1200 and the cover housing 1300 fit together in a single orientation. For example, the base housing 1200 further includes protrusions 1212 and 1214 that interact with corresponding features of the cover housing 1300 as shown in FIG. 22. As illustrated in FIG. 22, the cover portion includes a notch 1312, an aperture 1314 and a stabilization arm 1316. In an assembled configuration, the protrusion 1212 of the base housing 1200 is received in the notch 1312, and the protrusion 1214 is received in the aperture 1314. When assembled, the stabilization arm 1316 rests on the main portion 1220 of the base housing 1200 for stability.

Figure 24:
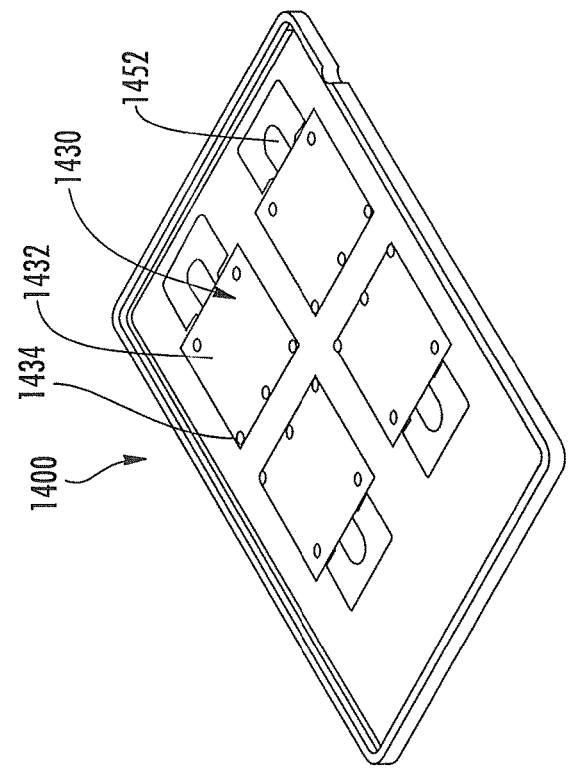
FIG. 24 is an assembled view of the sample cartridge of FIG. 23.
Figure 23:
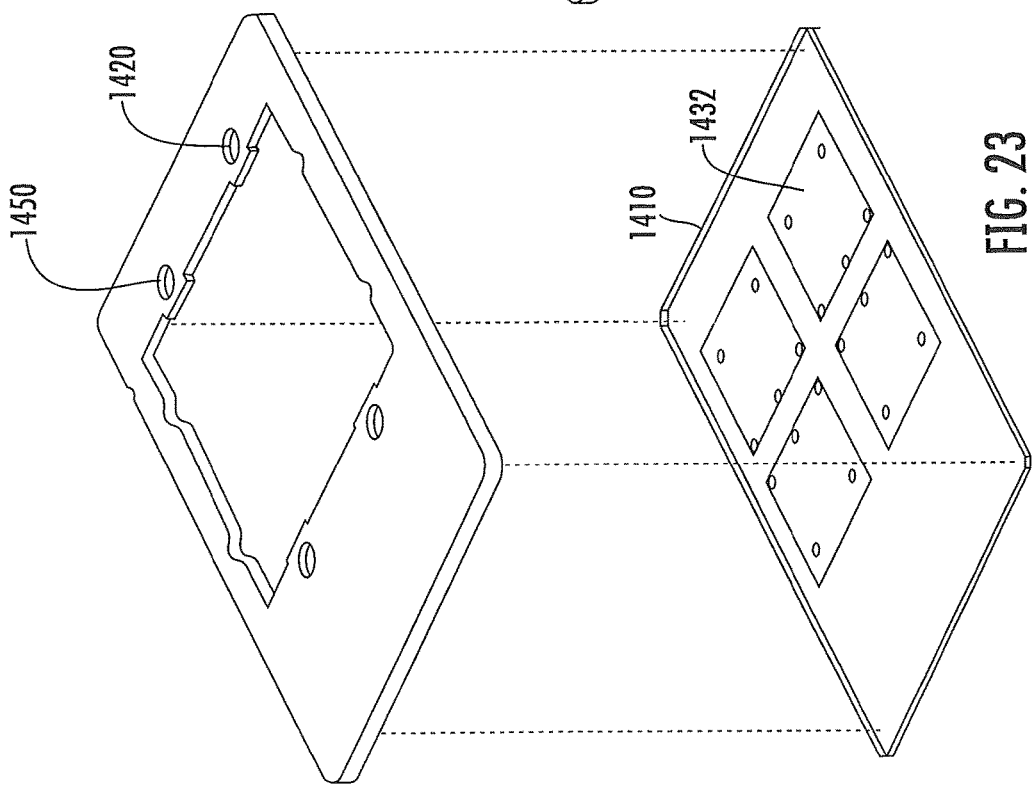
FIG. 23 is an exploded perspective view of a sample cartridge according to some embodiments.

As shown in FIGS. 23-24, the cartridge 1400 includes a glass plate 1410 having microscope cover slips 1432 affixed thereto, and a frame member 1420 that defines sample collection apertures 1450. The slides 1432 may be configured in a wedge-shape such that capillary action files the slides 1432 with the sample as a "self-preparing we smear" with a meta-chromatic stain, which may be preloaded into the sample areas 1430.

As illustrated, the apertures 1350 protrude from the cover housing member 1300 such that the apertures 1350 form a fluid connection with a corresponding feature in the cartridge 1400, such as the sample collection apertures 1450 to thereby fill the sample area 1430. For example, the apertures 1350 may protrude from the cover housing 1300 and fit into a corresponding well or other collection feature (such as the apertures 1450) on the cartridge 1400 to reduce or prevent leaking between the chambers 1210, the sealing features 1310 and the sample areas 1430.

Figure 25:
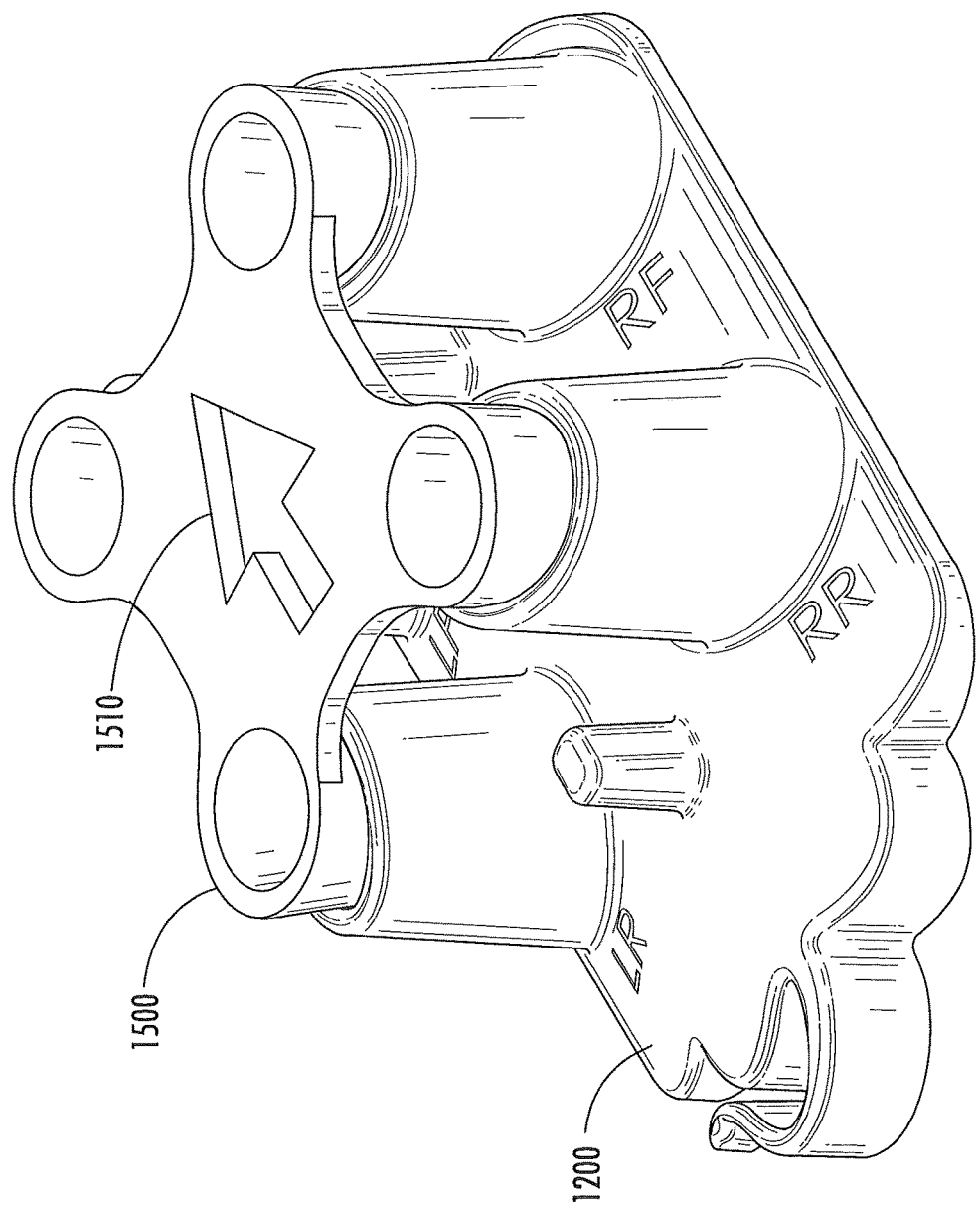
FIG. 25 is a front perspective view of the base housing of the collection and transfer device with a cover housing or plug according to some embodiments.

In some embodiments, the cover housing used for transfer may be substituted with a plug assembly that caps the fluid in the base housing for storage and/or transportation. In some embodiments the plug may be configured to allow stackability. In some embodiments, the fluid inside the base housing may be agitated before removing the plug assembly and replacing it with the cover housing used for transfer of the fluid to the cartridge. For example, as illustrated in FIG. 25, a cover housing or plug 1500 is optionally positioned on top of the base housing 1200 for storage and/or transport. The plug 1500 includes a directional arrow 1510 for indicating to the user the correct orientation of the plug 1500. Accordingly, the sample may be stored in the base housing 1200 and protected by the plug 1500, and the plug 1500 may be removed and the cover housing 1300 positioned thereon as described herein to transfer the sample to the cartridge 1400.

In some embodiments, various tracking techniques may be used to identify a particular sample with an animal. For example, the collection and transfer devices and/or the sample cartridges described herein may include a write-on label and/or a bar code label and/or an RFID tag for purposes of identifying the origin of the sample, such as a cow identification number.

In some embodiments, the sample cartridges described herein may be placed in a reader or imager for further analysis. When the sample comprises cells to be imaged and/or counted by the reader, the cells may be stained by a suitable stain, including fluorescent stains such as acridine orange (see, e.g., U.S. Pat. No. 3,883,247). In some embodiments, the cartridges described herein may use exogeneous targets as discussed below.

Microscopes

The present invention can be carried out with any suitable manual or automated microscope. Automated microscopes generally include a specimen support stage (e.g., configured for holding or securing a sample cartridge as described above), an objective lens, a camera operatively associated with the objective lens, at least one drive assembly operatively associated with said support stage and/or said objective lens. Examples of such microscopes include but are not limited to those described in U.S. Pat. Nos. 4,810,869; 5,483,055; 5,647,025; 5,790,710; 6,869,570; 7,141,773; and 8,014,583. In general, such apparatus includes a controller that is operatively associated with the camera and the at least one drive assembly which controller is configured through hardware and/or software to carry out an autofocus method as described herein (generally prior to acquisition of an image of the specimen or sample through the camera), typically through calculating a focus score. The focus score can be calculated by any suitable technique, including but not limited to those described in F. Groen et al., *A comparison of different focus functions for use in autofocus algorithms*, Cytometry 6, 81-91 (1985). Difference from the background, given a uniform background, can be calculated a number of ways, including but not limited to differences in contrast, gradient, and variance.

Exogeneous Targets.

General considerations for selecting the exogeneous target are as follows: The exogenous target should be visible by the particular optical system in use. This will depend on the magnification, excitation wavelength, size of field of view, etc. This will influence decisions on which size, shape, emission wavelengths, etc. of the texture. In addition, the exogeneous target should be distinguishable from the target objects. Preferably, the exogeneous target reside at substantially the same (or a known distance from) the focal plane of the target objects (e.g., be mixed with a biological sample suspected of containing cells to be imaged and/or counted, and/or placed in the same chamber as will contain a biological sample comprising cells to be imaged and/or counted). The exogenous target should be of a size, shape, and number so as to not substantially obscure the view of the intended target objects, such as cells to be imaged and/or counted. And, the exogenous target should provide sufficient contrast with an empty field of view so as to provide an adequate focal peak and allow for reliable, reasonably rapid, and/or robust focusing.

The exogenous targets may be formed of any suitable material, including organic polymers, inorganic materials (including crystalline materials, amorphous materials, metals, etc.) and composites thereof.

The exogenous targets may be contained loosely within the chamber, fixed to one wall of the chamber, or surface to be imaged (e.g., by adhesive, by electrostatic, hydrophilic, or hydrophobic interaction, covalent bond directly or through a linking group, etc.), and/or formed on one wall of the chamber (e.g., by molding, etching, painting, silk-screening, lithography, etc.).

The exogenous targets may be opaque or transparent. When transparent the targets may be "tinted" so as to transmit light therethrough at a predetermined wavelength (for example, so that they appear red, green, blue, yellow, etc., to a human observer).

The exogenous targets may be regular or irregular in shape (for example, cylinders, spheres, cubes, pyramids, prisms, cones, rods, etc.). In some embodiments, the targets have an average diameter of from 0.1, 0.5 or 1 micrometers up to 2, 5, or 10 micrometers.

The number of exogenous targets is not critical, but in some embodiments the speed of the autofocus process can be increased by increasing, at least to a point, the number of exogenous targets in the chamber so that the targets are readily located in the automated microscope. Where a plurality of targets are included in the sample chamber (e.g., 2, 4, 6, 8 or 10 targets, up to 100, 200, 400, 600 or 800 exogenous targets, or more), in some embodiments that plurality preferably consists of or consists essentially of targets having substantially the same size, shape, and optical characteristics.

In some embodiments, the targets are beads, such as fluorescent microbeads. Such microbeads are commonly available and used for calibrating flow cytometers or fluorescent microscopes (see, e.g., U.S. Pat. Nos. 4,698,262; 4,714,682; and 4,868,126).

The targets are preferably optically distinguishable from cells to be counted (and hence would not be useful as calibration standards for the particular cells to be counted and/or imaged by the methods described herein). Optically distinguishable may be achieved by any suitable technique, such as by utilizing targets of a different and distinguishable shape from the cells to be counted, by utilizing targets that emit, transmit, and/or reflect light at a different wavelength from the cells to be counted when under the same illumination conditions, and combinations thereof.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A collection and transfer assembly comprising:
   a collection device comprising:
      a base housing member having at least two chambers; and a cover housing member having at least two housing apertures therein, the cover housing member being configured to cover the base housing member such that each of the at least two housing apertures are positioned in fluid communication with a corresponding one of the at least two chambers, the cover housing member further comprising a cartridge holding interface; and a sample cartridge configured to be positioned on the cover housing member, the sample cartridge comprising:
a cartridge wall;
at least two sample areas comprising:
a portion of the cartridge wall; and
an optically transparent or translucent slide on the cartridge wall; and
at least two cartridge apertures, each of the two cartridge apertures being configured to receive a fluid from a respective one of the at least two chambers via a corresponding one of the at least two housing apertures such that the fluid flows between and is retained in a respective one of the at least two sample areas of the sample cartridge by a respective portion of the cartridge wall and the optically transparent or translucent slide,
wherein the cartridge holding interface on the cover housing member is configured to releasably engage with the sample cartridge such that the cartridge together with the cartridge slide is releasably retained by the cartridge holding interface of the cover housing member.

2. The collection and transfer assembly of claim 1, wherein each optically transparent or translucent slide of the at least two sample areas of the sample cartridge face away from the cover housing member, and the at least two cartridge apertures are on a side of the sample cartridge opposite the optically transparent or translucent slide and fluidly connect a respective one of the at least two housing apertures to a respective one of the at least two sample areas.

3. The collection and transfer assembly of claim 1, wherein each optically transparent or translucent slide of the sample cartridge face toward the cover housing member, and the at least two cartridge apertures are on a same side of the sample cartridge as the optically transparent or translucent slide opposite the cartridge wall and fluidly connect a respective one of the at least two housing apertures to a respective one of the at least two sample areas.

4. The collection and transfer assembly of claim 1, wherein the cartridge holding interface comprises a retaining wall or retaining pins configured to abut an outer perimeter of the cartridge.

5. The collection and transfer assembly of claim 4, wherein the cartridge holding interface further comprises at least one notch and/or groove that is configured to engage a corresponding notch and/or groove on the cartridge.

6. The collection and transfer assembly of claim 4, wherein the cartridge holding interface further comprises at least one hook member that is configured to engage and retain an edge portion of the cartridge.

7. The collection and transfer assembly of claim 1, wherein the cartridge holding interface is configured to interface with the cartridge in a single orientation.

8. The collection and transfer assembly of claim 1, wherein the base housing member and the cover housing member comprises cooperating sealing members that are configured to seal each of the at least two chambers.

9. The collection and transfer assembly of claim 8, wherein the cooperating sealing members comprise a base sealing feature between the at least two chambers on the base housing member, and a cover sealing feature on the cover housing member configured to engage with the base sealing feature and to thereby fluidly seal each of the at least two chambers.

10. The collection and transfer assembly of claim 9, wherein one of the base sealing feature and the cover sealing feature comprises a groove and the other of the base sealing feature and the cover sealing feature comprises a ridge that is configured to be received in the groove and form a snug fit.

11. The collection and transfer assembly of claim 8, wherein the at least two chambers overlap a central portion and a perimeter portion of the base housing member, and the chambers comprise a wall that has a height that is higher in the central portion than at the perimeter portion.

12. The collection and transfer assembly of claim 1, wherein each of the at least two chambers comprises wall portion that extends away from the base housing member and defines the chamber and, in an assembled position, is configured to extend into a corresponding sealing feature on the cover housing member to seal a sample therein.

13. The collection and transfer assembly of claim 12, wherein the base housing member comprises a central portion and a perimeter portion, and the wall portion of the plurality of chambers has a height that is higher in the central portion than at the perimeter portion of the base housing member.

14. The collection and transfer assembly of claim 12, wherein the at least two chambers comprises an fluid transfer feature comprising a protrusion having the housing aperture therein that is configured to fluidly transfer a sample from one of the respective at least two chambers to a corresponding sample area of a sample cartridge.

15. The collection and transfer assembly of claim 14, wherein the housing aperture of the fluid transfer feature is configured to fit inside a corresponding well of the sample cartridge.

16. The collection and transfer assembly of claim 1, further comprising a label, bar code and/or RFID that identifies an origin of a sample on the cartridge or on the collection device.

17. The collection and transfer assembly of claim 1, further comprising a plurality of exogeneous targets in the at least one sample area, wherein said exogenous targets are particles.

18. The collection and transfer assembly of claim 17, wherein said exogenous targets have an average diameter of from 0.1 micrometers up to 10 micrometers.

19. The collection and transfer assembly of claim 17, wherein said exogenous targets are fluorescent.

20. The collection and transfer assembly of claim 17, wherein said exogenous targets:
fluoresce at a peak absorption wavelength of at least 420 nanometers and at not more than 540 nanometers;
fluoresce at a peak emission wavelength of at least 450 nanometers and not more than 590 nanometers;
and wherein said peak absorption wavelength and said peak emission wavelength differ by at least 10 nanometers.

21. The collection and transfer assembly of claim 1, wherein the cover housing comprises a housing wall that abuts and is parallel to the optically transparent or translucent slide.

22. The collection and transfer assembly of claim 1, wherein the cover housing comprises a housing wall that abuts and is parallel to the cartridge wall.

23. The collection and transfer assembly of claim 1, wherein the cover housing engages the base housing with a snap-fit interface.

24. The collection and transfer assembly of claim 1, wherein each of the at least two chambers comprises a sidewall, and the respective sidewalls of each of the at least two chambers are spaced apart from one another.

25. The collection and transfer assembly of claim 1, further comprising a plug member that is configured to be positioned over the base housing when the cover housing is removed and to seal the fluid in the at least one chamber of the base housing.

26. The collection and transfer assembly of claim 1, wherein the optically transparent or translucent slide and the portion of the cartridge wall of each of the sample areas are configured such that fluid flows by capillary flow between the cartridge wall and the optically transparent or translucent slide.

* * * * *

UNITED STATES PATENT AND TRADEMARK OFFICE
CERTIFICATE OF CORRECTION

PATENT NO. : 10,426,445 B2  Page 1 of 1
APPLICATION NO. : 14/394900
DATED : October 1, 2019
INVENTOR(S) : Calderwood et al.

It is certified that error appears in the above-identified patent and that said Letters Patent is hereby corrected as shown below:

On the Title Page

Item (72) Inventors: Please add: Jaspar Pollard, Durham, NC (US)

Signed and Sealed this
Eighteenth Day of February, 2020

Andrei Iancu
*Director of the United States Patent and Trademark Office*